US007931900B2

(12) United States Patent
Christie et al.

(10) Patent No.: US 7,931,900 B2
(45) Date of Patent: Apr. 26, 2011

(54) METHOD FOR THE TREATMENT OF MULTIPLE SCLEROSIS BY INHIBITING IL-17 ACTIVITY

(75) Inventors: Mark Ian Christie, Newmarket (GB); Richard James Mead, Sheffield (GB); Martyn Kim Robinson, High Wycombe (GB); Stephen Edward Rapecki, Burnham (GB)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 12/277,030

(22) Filed: Nov. 24, 2008

(65) Prior Publication Data

US 2009/0191200 A1 Jul. 30, 2009

Related U.S. Application Data

(63) Continuation of application No. 10/580,164, filed as application No. PCT/GB2004/004850 on Nov. 16, 2004, now abandoned.

(30) Foreign Application Priority Data

Nov. 21, 2003 (GB) .................................. 0327181.4
Jul. 30, 2004 (GB) .................................. 0417115.3

(51) Int. Cl.
*A61K 39/395* (2006.01)
(52) U.S. Cl. ............... 424/134.1; 424/130.1; 424/139.1; 424/178.1
(58) Field of Classification Search ........................ None
See application file for complete search history.

(56) References Cited

U.S. PATENT DOCUMENTS

| | | | |
|---|---|---|---|
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,596,556 A | 6/1986 | Morrow et al. |
| 4,790,824 A | 12/1988 | Morrow et al. |
| 4,941,880 A | 7/1990 | Burns |
| 4,946,778 A | 8/1990 | Ladner et al. |
| 4,980,286 A | 12/1990 | Morgan et al. |
| 5,064,413 A | 11/1991 | McKennon et al. |
| 5,219,996 A | 6/1993 | Bodner et al. |
| 5,223,409 A | 6/1993 | Ladner et al. |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,403,484 A | 4/1995 | Ladner et al. |
| 5,427,908 A | 6/1995 | Dower et al. |
| 5,516,637 A | 5/1996 | Huang et al. |
| 5,571,698 A | 11/1996 | Ladner et al. |
| 5,580,717 A | 12/1996 | Dower et al. |
| 5,585,089 A | 12/1996 | Queen et al. |
| 5,658,727 A | 8/1997 | Barbas et al. |
| 5,677,425 A | 10/1997 | Bodner et al. |
| 5,698,426 A | 12/1997 | Huse |
| 5,733,743 A | 3/1998 | Johnson et al. |
| 5,738,996 A | 4/1998 | Hodges et al. |
| 5,750,753 A | 5/1998 | Kimae et al. |
| 5,780,225 A | 7/1998 | Wigler et al. |
| 5,807,683 A | 9/1998 | Brenner |
| 5,821,047 A | 10/1998 | Garrard et al. |
| 5,969,108 A | 10/1999 | McCafferty et al. |
| 6,043,344 A | 3/2000 | Jacobs et al. |
| 6,274,711 B1 | 8/2001 | Golstein et al. |
| 2003/0049255 A1 | 3/2003 | Sims et al. |

FOREIGN PATENT DOCUMENTS

| | | |
|---|---|---|
| EP | 0 392 745 B1 | 11/1994 |
| EP | 0 948 544 B1 | 5/2003 |
| WO | 86/01533 A1 | 3/1986 |
| WO | 90/02809 A1 | 3/1990 |
| WO | 91/10737 A1 | 7/1991 |
| WO | 92/01047 A1 | 1/1992 |
| WO | 92/02551 A1 | 2/1992 |
| WO | 92/18619 A1 | 10/1992 |
| WO | 92/22853 A1 | 12/1992 |
| WO | 93/08829 A1 | 5/1993 |
| WO | 93/11236 A1 | 6/1993 |
| WO | 95/15982 A2 | 6/1995 |
| WO | 95/18826 A2 | 7/1995 |
| WO | 95/20401 A1 | 8/1995 |
| WO | 97/04097 A2 | 2/1997 |
| WO | 98/25971 A1 | 6/1998 |
| WO | 99/15549 A3 | 4/1999 |
| WO | 01/46420 A2 | 6/2001 |
| WO | 2004/042009 A3 | 5/2004 |
| WO | 2004/083249 A2 | 9/2004 |
| WO | 2005/000897 A2 | 1/2005 |
| WO | 2005/003169 A2 | 1/2005 |
| WO | 2005/003170 A3 | 1/2005 |
| WO | 2005/003171 A3 | 1/2005 |
| WO | 2007/070750 A1 | 6/2007 |
| WO | 2008/067223 A2 | 6/2008 |

OTHER PUBLICATIONS

Kotake et al., IL-17 in synovial fluids from patients with rheumatoid arthritis is a potent stimulator of osteoclastogenesis, The Journal of Clinical Investigation, 103:1345-1352 (1999). Chabaud et al., "Contribution of Interleukin 17 to Synovium Matrix Destruction in Rheumatoid Arthritis", Cytokine, 12:1092-1099 (2000).
Aggarwal, S. et al., "Interleukin-23 promotes a distinct CD4 T cell activation state characterized by the production of interleukin-17", J. of Biological Chem, 278(3), 2003, 1910-1914.
Ames, R. S. et al., "Conversion of murine Fabs isolated from a combinatorial phage display library to full length immunoglobulins", J. Immunol. Methods, vol. 184, 1995, 177-186.
Babcock, J. S. et al., "A novel strategy for generating monoclonal antibodies from single, isolated lymphocytes producing antibodies of defined specificities", Proc. Natl. Acad. Sci. USA, vol. 93, 1996, 7843-7848.
Baker, D. et al., "Induction of chronic relapsing experimental allergic encephalomyelitis in biozzi mice", Journal of Neuroimmunology, vol. 28, 1990, 261-270.

(Continued)

*Primary Examiner* — Prema Mertz
(74) *Attorney, Agent, or Firm* — McDonnell Boehnen Hulbert & Berghoff LLP

(57) ABSTRACT

The present invention provides a method for the treatment and/or prophylaxis of multiple sclerosis (MS) comprising administering a therapeutically effective amount of an inhibitor of IL-17 activity.

4 Claims, 13 Drawing Sheets

OTHER PUBLICATIONS

Figure 1:
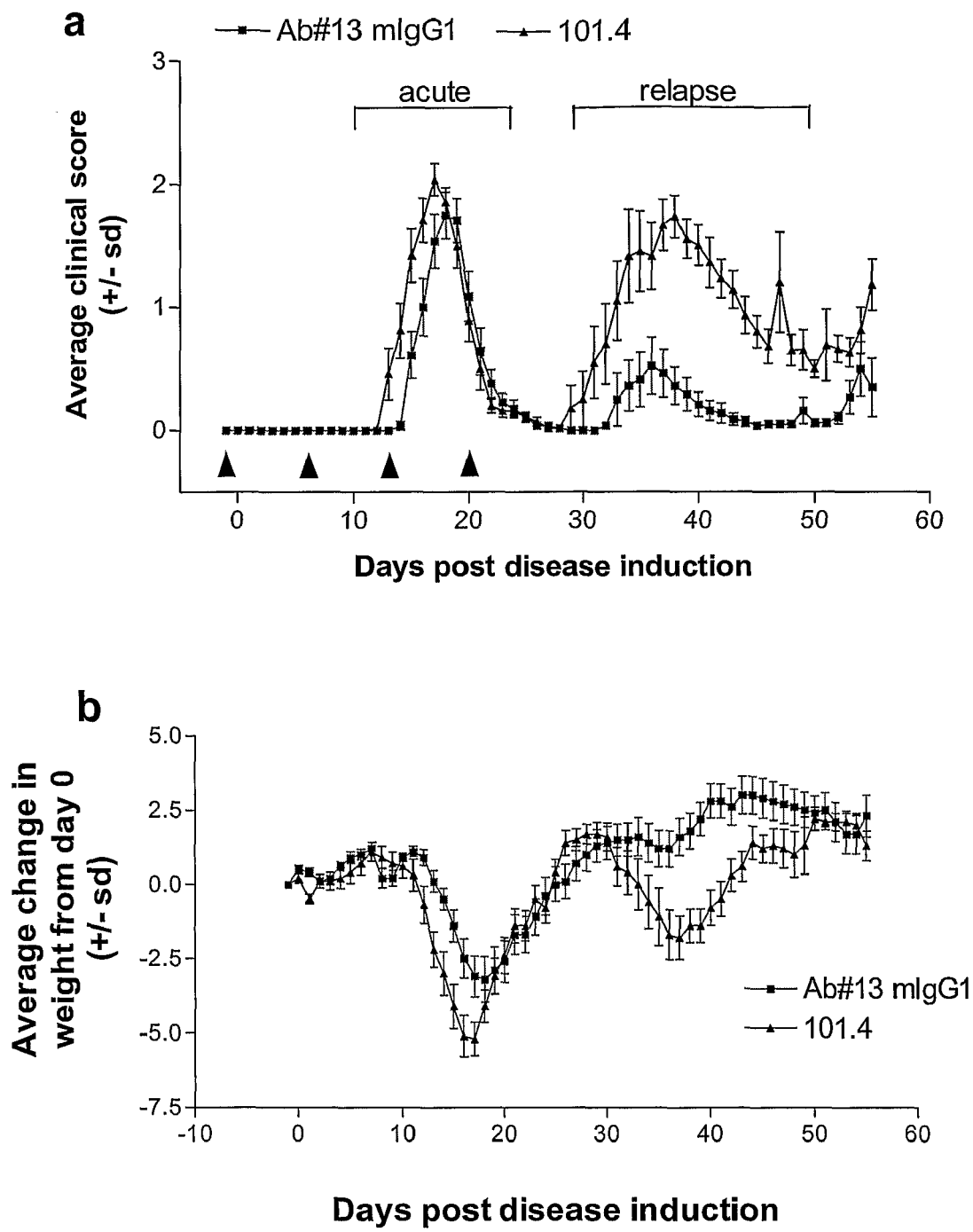

Bollard, C. et al., "Adapting a transforming growth factor B-related tumor protection strategy to enhance antitumor immunity", Blood, 99(9), 2002, 3179-3187.

Brinkman, U. et al., "Phage display of disulfide-stabilized Fv fragments", J. Immunol. Methods, vol. 182, 1995, 41-50.

Burns, J. A. et al., "Selective reduction of disulfides by tris(2-carboxyethyl)phophine", J. Org. Chem., vol. 56, 1991, 2648-2650.

Burton, D. R. et al., "Human antibodies for combinatorial libraries", Advances in Immunology, vol. 57, 1994, 191-280.

Carrell, T. et al., "A novel procedure for the synthesis of libraries containing small organic molecules", Angew. Chem Inc. Ed. Engl., 33(20), 1994, 2059-2061.

Chapman, A. P., "PEGylated antibodies and antibody fragments for improved therapy: a review", Advanced Drug Delivery Reviews, vol. 54, 2002, 531-545.

Cho, C.Y. et al., "An unnatural biopolymer", Science, vol. 261, 1993, 1303-1305.

Chung, D. R. et al., "CD4+ T cells regulate surgical and postinfectious adhesion formation", J. Exp. Med., 195(11), 2002, 1471-1478.

Cole, S. P. C. et al., "The EBV-hybridoma technique and its application to human lung cancer", Monclonal Antibodies and Cancer Therapy, 1985, 77-96.

Copray, S. et al., "Deficient p75 low-affinity neurotrophin receptor expression exacerbates experimental allergic encephalomyelitis in C57/BL6 mice", Journal of Neuroimmunology, vol. 148, 2004, 41-53.

Cull, M. G. et al., "Screening for receptor ligands using large libraries of peptides linked to the C terminus of the lac repressor", Porc. Natl. Acad. Sci. USA, vol. 89, 1992, 1865-1869.

Cwirla, S. E. et al., "Peptides on phage: a vast library of peptides for identifying ligands," Proc. Natl. Acad. Sci. vol. 87, 1990, 6378-6382.

Devlin, J.J. et al., "Random peptide libraries: a source of specific protein binding molecules," Science, vol. 249, 1990, 404-406.

Dewitt, S.H. et al., "Diversomers": an approach to nonpeptide, nonoligomeric chemical diversity, Pro. Natl. Acad. Sci. USA, vol. 90, 1993, 6909-6913.

Dubowchik, G.M. et al., "Receptor-mediated and enzyme-dependent targeting of cytotoxic anticancer drugs," Pharmacology and Therapeutics, vol. 83, 1999, 67-123.

Dumont, F.J. "IL-17 cytokine/receptor families: emerging targets for the modulation of inflammatory responses," Expert Opin. Ther. Patents, vol. 13(3), 2003, 287-303.

Ellison, D. et al., "Photoreduction of monoclonal antibodies for conjugation and fragmentation," Biotechniques, vol. 28, 2000, 324-326.

Erb, E. et al., "Recursive deconvolution of combinatorial chemical libraries," Proc. Natl. Acad. Sci. USA, vol. 91, 1994, 11422-11426.

Felici, F., "Selection of antibody ligands from a large library of oligopeptides expressed on a multivalent exposition vector," J. Mol. Biol., vol. 222, 1991, 301-310.

Ferreti, F. et al., "IL-17, produced by lymphocytes and neutrophils, is necessary for lipopolysaccharide-induced airway neutrophilia: IL-15 as a possible trigger," Journal of Immunology, vol. 170, 2003, 2106-2112.

Fodor, S.P.A. et al., "Multiplexed biochemical assays with biological chips," Nature, vol. 364, 1993, 555-556.

Fossiez, F. et al., "Interleukin-17," Int. Rev. Immunol., vol. 16, 1998, 541-551.

Gallop, M. A. et al., "Applications of combinatorial technologies to drug discovery. 1. Background and peptide combinatorial libraries," J. Med. Chem., vol. 37(9), 1994, 1233.

Getz, E. B. et al., "A comparison between the sulfhydryl reductants tris(2-carboxyethyl)phosphine and dithiothreitol for use in protein biochemistry," Analytical Biochemistry, vol. 273, 1999, 73-80.

Goodin, D.S. et al., "Disease modifying therapies in multiple sclerosis; Report of the therapeutics and technology assessment subcommittee of the American Academy of Neurology and the Ms Council for Clinical Practice Guidelines," American Academy of Neurology, vol. 58(2), 2002, 169-178.

Han, J.C. et al., "A procedure for quantitative determination of tris(2-carboxyethyl)phosphine, an orderless reducing agent more stable and effective than dithiothreitol," Anayltical Biochemistry, vol. 220, 1994, 5-10.

Hellstrom, K.E. et al., "Antibodies for drug delivery," Controlled Drug Delivery, 2nd Ed, Robinson, J.R., et al. (Eds.), 1987, 623-653.

Hoshida, T. et al., "Gene therapy for pancreatic cancer using an adenovirus vector encoding soluble flt-1 vascular endothelial growth factor receptor," Pancreas, vol. 25(2), 2002, 111-121.

Houghten, R.A., et al., "The use of synthetic peptide combinatorial libraries for the identification of bioactive peptides," Bio/Techniques, vol. 13(3), 1992, 412-421.

Humphreys, D.P. et al., "A plasmid system for optimization of Fab' production in Escherichia coli; importance of balance of heavy chain and light chain synthesis," Protein Expression and Purification, vol. 26, 2002, 309-320.

Ikuno, Y., "An in vivo gene therapy approach for experimental proliferative vitreoretinopathy using the truncated platelet-derived growth factor a receptor," Invest Opthalmol Vis. Sci., vol. 43(7), 2002, 2406-2411.

Jacoby, D.R. et al., "Hybrid vectors: a new generation of virus-based vectors designed to control the cellular fate of delivered genes," Gene Therapy, vol. 4, 1997, 1282-1283.

Kettleborough, C.A. et al., "Isolation of tumor cell-specific single chain Fv from immunized mice using phage-antibody libraries and the re-construction of whole antibodies from these antibody fragments," Eur. J. Immunol, vol. 24, 1994, 952-958.

Kochanek, S., "High-capacity adenoviral vectors for gene transfer and somatic gene therapy," Human Gene Therapy, vol. 10, 1999, 2451-2459.

Köhler, G. et al., "Continuous cultures of fused cells secreting antibody of predefined specificity," Nature, vol. 256, 1975, 495-497.

Kozbor, D. et al., "The production of monoclonal antibodies from human lymphocytes," Immunology Today, vol. 4 (3), 1983, 72-79.

Lam, L.S., "Application of combinatorial library methods in cancer research and drug discovery," Anti-cancer Drug Des., vol. 12, 1997, 145-167.

Lam, K.S. et al., "A new type of synthetic peptide library for identifying ligand-binding activity," Nature, vol. 354, 1991, 82-84.

Leach, S.J. et al., "The electrolytic reduction of proteins," Div. Protein Chem. vol. 4(1), 1965, 23-27.

Lee, E.J., et al., "Adenovirus-directed expression of dominant negative estrogen receptor induces apoptosis in breast cancer cells and regression," Mol. Med., vol. 7(11), 2001, 773-782.

Lock, C. et al., "Gene-microarray analysis of multiple sclerosis lesions yields new targets validated in autoimmune encephalomyelitis," Nature Medicine, vol. 8(5), 2002, 500-508.

Lubberts, E. et al., "IL-1 independent role of IL-17 in synovial inflammation and joint destruction during collagen-induced arthritis," J. Immunol, vol. 167, 2001, 1004-1013.

Mastusevicius, D. et al., "Interleukin-17 mRNA expression in blood and CSF mononuclear cells is augmented in multiple sclerosis," Multiple Sclerosis, vol. 5, 1999, 101-104.

Miller, D. et al., "Use of retroviral vectors for gene transfer and expression," Meth. Enzymol, vol. 217, 1993, 581-599.

Milstein, C. et al., "Hybrid hybridomas and their use in immunohistochemistry," Nature, vol. 305, 1983, 537-539.

Pelidou, S.H. et al., "Enchancement of acute phase and inhibition of chronic phase of experimental autoimmune neuritis in Lewis rats by intranasal administration of recombinant mouse interleukin 17: potential immunoregulatory role, "Experimental Neurology, vol. 163, 2000, 2000-2005.

Persic, L. et al., "An integrated vector system for the eukaryotic expression of antibodies or their fragments after selection from phage display libraries," Gene, vol. 187, 1997, 9-18.

Reynolds, P.N. et al., "Chimeric viral vectors-the best of both worlds?," Molecular Medicine Today, 1999, 25-31.

Robbins, P.D. et al., "Viral vectors for gene therapy," Pharmacol Ther., vol. 80(1), 1998, 35-47.

Rüegg, U.T. et al., "Reductive cleavage of cystine disulfides with tributylphosphine," Methods in Enzymology, vol. 47, 1977, 111-126.

Scott, J.K. et al., "Searching for peptide ligands with an epitope library," Science, vol. 249, 1990, 386-390.

Seitz, U. et al., "Preparation and evaluation of the rhenium-188 labelled anti-NCA antigen monoclonal antibody BW 250/183 for radioimmunotherapy of leukaemia," Euro. J. Nuclear Medicine, vol. 26(10), 1999, 1265-1273.

Singh, R. et al., "Reagents for rapid reduction of disulfide bonds," Methods in Enzymology, vol. 251, 1995, 167-173.

t'Hart, B.A. et al., "The use of animal models to investigate the pathogenesis of neuroinflammatory disorders of the central nervous system," Current Opinion in Neurology, vol. 16, 2003, 375-383.

Thorpe, P.E. et al., "The preparation and cytotoxic properties of antibody-toxin conjugates," Immunol Rev., vol. 62, 1982, 119-158.

Traunecker, A. et al., "Bispecific single chain molecules (Janusins) target cytotoxic lymphocytes on HIV infected cells," EMBO J., 10(12), 1991, 3655-3659.

Verma, R. et al., "Antibody engineering: comparison of bacterial, yeast, insect and mammalian expression systems," Journal of Immunological Methods, vol. 216, 1998, 165-181.

Wu, G.Y. et al., "Receptor-mediated in vitro gene transformation by a soluble DNA carrier system," J. Biol. Chem., 262 (10), 1987, 4429-4432.

Yao, Z. et al., "Molecular characterization of the human interleukin (IL)-17 receptor," Cytokine, 9(11), 1997, 794-800.

Yao, Z. et al., "Herpesvirus saimiri encodes a new cytokine, IL-17, which binds to a novel cytokine receptor," Immunity, vol. 3, 1995, 811-821.

Yao, Z. et al., "Human IL-17: a novel cytokine derived from T cells," Journal of Immunology, vol. 155, 1995, 5483-5486.

Zuckermann, R.N. et al., "Discovery of nanomolar ligands for 7-transmembrane G-protein-coupled receptors from a diverse N-(substituted)glycine peptoid library," J. Med. Chem., vol. 37, 1994, 2678-2685.

Chuntharapai et al., Methods in Enzymology, vol. 288, 15-27, 1997.

Yazaki et al., "Humanization of the anti-CEA T84.66 antibody based on crystal structure data", Protein Engineering, Design & Selection, 2004, 17(5), 481-489.

Zhang et al., "Induction of Experimental Autoimmune Encephalomyelitis in IL-12 Receptor-β-Deficient Mice: IL-12 Responsiveness Is Not Required in the Pathogenesis of Inflammatory Demyelination in the Central Nervous System", The Journal of Immunology, 2003, 170(4), 2153-2160.

Okuda et al., "IL-6 plays a crucial role in the induction phase of myelin oligodendrocyte glycoprotein 35-55 induced experimental autoimmune encephalomyelitis", Journal of Neuroimmunology 101, 1999, 188-196.

Burchill et al., "Inhibition of Interleukin-17 Prevents the Development of Arthritis in Vaccinated Mice Challenged with Borrelia burgdorferi", Infection and Immunity, 2003, 71(6), 3437-3442.

Witowski et al., "IL-17 Stimulates Intraperitoneal Neutrophil Infiltration Through the Release of GROα Chemokine from Mesothelial", The Journal of Immunology, 2000, 5814-5821.

Bush et al., "Reduction of Joint Inflammation and Bone Erosion in Rat Adjuvant Arthritis by Treatment with Interleukin-17 Receptor IgG1 Fc Fusion Protein", Arthritis & Rheumatism, 2002, 46(3), 802-805.

Haak et al., "IL-17A and IL-17F do not contribute vitally to autoimmune neuro-inflammation in mice", The Journal of Clinical Investigation, 2009, 119(1), 61-69.

Product data sheet for anti-IL-17 antibody TC11-18H10 obtained from BioLegend's (manufacturer) website, references cited as late as 2007, 2 sheets.

Özenci et al., "Cytokines in multiple sclerosis: methodological aspects and pathogenic implications", Multiple Sclerosis, 2002, vol. 8, 396-404.

Cua et al., "Interleukin-23 rather than interleukin-12 is the critical cytokine for autoimmune inflammation of the brain", Nature, 2003, vol. 21, 744-748.

Jovanovic et al., "IL-17 Stimulates the Production and Expression of Proinflammatory Cytokines, IL-β and TNF-α by Human Macrophages", The Journal of Immunology, 1998, vol. 160, 3513-3521.

Aggarwal et al., "IL-17: prototype member of an emerging cytokine family", Journal of Leukocyte Biology, 2002, vol. 71, 1-8.

Joosten et al., "Dual Role of IL-12 in Early and Late Stages of Murine Collagen Type II Arthritis", The Journal of Immunology, 1997, vol. 159, 4094-4102.

Constantinescu et al., "Antibodies Against IL-12 Prevent Superantigen-Induced and Spontaneous Relapses of Experimental Autoimmune Encephalomyelitis", The Journal of Immunology, 1998, vol. 161, 5097-5104.

Tarner et al., "Gene therapy in autoimmune disease", Current Opinion in Immunology, 2001, vol. 13, 676-682.

Jonker et al., "Autoimmunity in Non-Human Primates: the Role of Major Histocompatibility Complex and T Cells, and Implications for Therapy", Human Immunology, 1991, vol. 32, 31-40.

Singh et al., "The Paradigm of Th1 and Th2 Cytokines", Immunologic Research, 1999, vol. 20, 147-161.

Fossiez et al., "T Cell Interleukin-17 Induces Stromal Cells to Produce Proinflammatory and Hematopoietic Cytokines", J. Exp. Med., 1996, vol. 183, 2593-2603.

Van Kooten et al., "Interleukin-17 Activates Human Renal Epithelial Cells In Vitro and Is Expressed During Renal Allograft Rejection", J. Am. Soc. Nephroi., 1998, vol. 9, 1526-1998.

Becher et al., "Experimental autoimmune encephalitis and inflammation in the absence of interleukin-12", J. Clin. Invest., 2002, vol. 110, 493-497.

Becher et al., "IL-23 produced by CNS-resident cells controls T-cell encephalitogenicity during the effector phase of experimental autoimmune encephalomyelitis", J. Clin. Invest., 2003, vol. 112, 1186-1191.

Nakae et al., "Antigen-Specific T Cell Sensitization Is Impaired in IL-17 Deficient Mice, Causing Suppression of Allergic Cellular and Humoral Responses", Immunity, 2002, vol. 17, 375-387.

Nakae et al., "Suppression of Immune Induction of Collagen-Induced Arthritis in IL-17-Deficient Mice", The Journal of Immunology, 2003, vol. 171, 6173-6177.

Tompkins et al., "An array of possibilities for multiple sclerosis", Nature Medicine, 2002, 8(5), 451-453.

Wiendl et al., "Therapeutic Approaches in Multiple Sclerosis: Lessons from Failed and Interrupted Treatment Trials", Biodrugs, 2002, 16(3), 183-200.

Blažek et al., "The Production and Application of Single-Chain Antibody Fragments", Folia Microbiol., 2003, 48(5), 687-698.

Langrish et al., "IL-23 drives a pathogenic T cell population that induces autoimmune inflammation", J. Exp. Med., 2005, 201(2), 233-240.

Chen et al., "Anti-IL-23 therapy inhibits multiple inflammatory pathways and ameliorates autoimmune encephalomyelitis", The Journal of Clinical Investigation, 2006, 116(5), 1317-1326.

Brekke et al., "Therapeutic antibodies for human disease at the dawn of the twenty-first century", Nature Reviews, 2003, vol. 2, 52-62.

Hudson et al., "Engineered antibodies", Nature Medicine, 2003, 9(1), 129-134.

Morrissey et al., "The significance of brain magnetic resonance imaging abnormalities at presentation with clinically isolated syndromes suggestive of multiple sclerosis", Brain, 1993, vol. 116, 135-146.

Dalton et al., "Application of the New McDonald Criteria to Patients with Clinically Isolated Syndromes Suggestive of Multiple Sclerosis", Ann. Neurol. 2002, vol. 52, 47-53.

Eriksson et al., "Long-term follow up of patients with clinically isolated syndromes relapsing-remitting and secondary progressive multiple sclerosis", Multiple Sclerosis, 2003, vol. 9, 260-272.

Miller et al., "Clinically isolated syndromes suggestive of multiple sclerosis part I: natural history, pathogenesis, diagnosis, and prognosis", Lancet Neurol., 2005, vol. 4, 281-288.

Rader et al., "The Rabbit Antibody Repertoire as a Novel Source for the Generation of Therapeutic Human Antibodies", The Journal of Biological Chemistry, 2000, 275(18), 13668-13676.

Lankford et al., "A unique role for IL-23 in promoting cellular immunity", Journal of Leukocyte Biology, 2003, vol. 73, 49-56.

Gijbels et al., "Administration of Neutralizing Antibodies to Interleukin-6 (IL-6) Reduces Experimental Autoimmune Encephalomyelitis and Is Associated with Elevated Levels of IL-6 Bioactivity in Central Nervous System and Circulation", Molecular Medicine, 1995, 1(7), 795-805.

Notice of Opposition by Eli Lilly and Company to European Patent No. EP 1 687 026 B1, issued on Feb. 16, 2009.

Notice of Opposition by Merck Serono SA to European Patent No. EP 1 687 026 B1, issued on Feb. 13, 2009.

Notice of Opposition by Schering Corporation to European Patent No. EP 1 687 026 B1, issued on Feb. 13, 2009.

Proprietors Response to Opposition Statements issued in European Patent No. EP 1 687 026 B1, dated Feb. 17, 2010.

EPO Summons to attend oral proceedings pursuant to Rule 115(1) EPC issued in European Patent No. EP 1 687 026 B1, dated Jul. 23, 2010.

Jackson et al., "Quantification of Myelin and Axon Pathology During Relapsing Progressive Experimental Autoimmune Encephalomyelitis in the Biozzi ABH Mouse", J. Neuropathol. Exp. Neurol., 2009, 68(6), 616-625.

Hampton et al., "An experimental model of secondary progressive multiple sclerosis that shows regional variation in gliosis, remyelination, axonal and neuronal loss", Journal of Neuroimmunology, 2008, vol. 201-201, 200-211.

Zargari et al., "Relationship between the clinical scoring and demyelination in central nervous system with total antioxidant capacity of plasma during experimental autoimmune encephalomyelitis development in mice", Neuroscience Letters, 2007, vol. 412, 24-28.

Hofstetter et al., "Therapeutic efficacy of IL-17 neutralization in murine experimental autoimmune encephalomyelitis", Cellular Immunology, 2005, vol. 237, 123-130.

Uyttenhove et al., "Anti-IL-17A Autovaccination Prevents Clinical and Histological Manifestations of Experimental Autoimmune Encephalomyelitis", Annals of the New York Academy of Sciences, 2007, vol. 1110, 330-336.

Siffrin et al., "In Vivo Imaging of Partially Reversible Th17 Cell-Induced Neuronal Dysfunction in the Course of Encephalomyelitis", Immunity, 2010, vol. 33, 424-436.

(a)

(b)

Figure 13

Seq ID No:1
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSC

Seq ID No:2
KRTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

Seq ID No: 3
KTTPPSVYPLAPGSAAQTNSMVTLGCLVKGYFPEPVTVTWNSGSLSSGVHTFPAVLQSDLYT
LSSSVTVPSSTWPSETVTCNVAHPASSTKVDKKIVPRDC

Seq ID No:4
DAAPTVSIFPPSSEQLTSGGASVVCFLNNFYPKDINVKWKIDGSERQNGVLNSWTDQDSKDS
TYSMSSTLTLTKDEYERHNSYTCEATHKTSTSPIVKSFNRGEC

SEQUENCE LISTING

<160> NUMBER OF SEQ ID NOS: 4

<210> SEQ ID NO 1
<211> LENGTH: 103
<212> TYPE: PRT
<213> ORGANISM: Homo sapiens

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val Glu Pro Lys Ser Cys
                100

<210> SEQ ID NO 2
<211> LENGTH: 108
<212> TYPE: PRT
<213> ORGANISM: Homo sapiens

<400> SEQUENCE: 2

Lys Arg Thr Val Ala Ala Pro Ser Val Phe Ile Phe Pro Pro Ser Asp
 1               5                  10                  15

Glu Gln Leu Lys Ser Gly Thr Ala Ser Val Val Cys Leu Leu Asn Asn
             20                  25                  30

Phe Tyr Pro Arg Glu Ala Lys Val Gln Trp Lys Val Asp Asn Ala Leu
         35                  40                  45

Gln Ser Gly Asn Ser Gln Glu Ser Val Thr Glu Gln Asp Ser Lys Asp
     50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
                 85                  90                  95

Ser Pro Val Thr Lys Ser Phe Asn Arg Gly Glu Cys
            100                 105

<210> SEQ ID NO 3
<211> LENGTH: 101
<212> TYPE: PRT
<213> ORGANISM: Mus musculus

<400> SEQUENCE: 3

Lys Thr Thr Pro Pro Ser Val Tyr Pro Leu Ala Pro Gly Ser Ala Ala
 1               5                  10                  15

Gln Thr Asn Ser Met Val Thr Leu Gly Cys Leu Val Lys Gly Tyr Phe
             20                  25                  30

Pro Glu Pro Val Thr Val Thr Trp Asn Ser Gly Ser Leu Ser Ser Gly
         35                  40                  45

Val His Thr Phe Pro Ala Val Leu Gln Ser Asp Leu Tyr Thr Leu Ser
     50                  55                  60

Ser Ser Val Thr Val Pro Ser Ser Thr Trp Pro Ser Glu Thr Val Thr
 65                  70                  75                  80

Cys Asn Val Ala His Pro Ala Ser Ser Thr Lys Val Asp Lys Lys Ile
                 85                  90                  95

Val Pro Arg Asp Cys
            100

<210> SEQ ID NO 4
<211> LENGTH: 105
<212> TYPE: PRT
<213> ORGANISM: Mus musculus
```

```
<400> SEQUENCE: 4

Asp Ala Ala Pro Thr Val Ser Ile Phe Pro Pro Ser Ser Glu Gln Leu
1               5                   10                  15

Thr Ser Gly Gly Ala Ser Val Val Cys Phe Leu Asn Asn Phe Tyr Pro
            20                  25                  30

Lys Asp Ile Asn Val Lys Trp Lys Ile Asp Gly Ser Glu Arg Gln Asn
        35                  40                  45

Gly Val Leu Asn Ser Trp Thr Asp Gln Asp Ser Lys Asp Ser Thr Tyr
    50                  55                  60

Ser Met Ser Ser Thr Leu Thr Leu Thr Lys Asp Glu Tyr Glu Arg His
65                  70                  75                  80

Asn Ser Tyr Thr Cys Glu Ala Thr His Lys Thr Ser Thr Ser Pro Ile
                85                  90                  95

Val Lys Ser Phe Asn Arg Gly Glu Cys
            100                 105
```

METHOD FOR THE TREATMENT OF MULTIPLE SCLEROSIS BY INHIBITING IL-17 ACTIVITY

This application is a continuation of U.S. patent application Ser. No. 10/580,164 filed on May 18, 2006, now abandoned which is a US national phase of International Application PCT/GB2004/004850 filed on Nov. 16, 2004, the disclosures of which are hereby incorporated by reference in their entirety.

The present invention relates generally to methods of treating multiple sclerosis and more specifically to the use of inhibitors of IL-17 activity for the manufacture of a medicament for the treatment of multiple sclerosis.

Interleukin 17 (IL-17), also known as CTLA-8 or IL-17A, is a pro-inflammatory cytokine which stimulates the secretion of a wide range of other cytokines from various non-immune cells. IL-17 is capable of inducing the secretion of IL-6, IL-8, PGE2, MCP-1 and G-CSF by adherent cells like fibroblasts, keratinocytes, epithelial and endothelial cells and is also able to induce ICAM-1 surface expression, proliferation of T cells, and growth and differentiation of CD34+ human progenitors into neutrophils when cocultured in presence of irradiated fibroblasts (Fossiez et al., 1998, Int. Rev. Immunol. 16, 541-551). IL-17 is predominantly produced by activated memory T cells and acts by binding to a ubiquitously distributed cell surface receptor (IL-17R) (Yao et al., 1997, Cytokine, 9, 794-800). A number of homologues of IL-17 have been identified which have both similar and distinct roles in regulating inflammatory responses. For a review of IL-17 cytokine/receptor families see Dumont, 2003, Expert Opin. Ther. Patents, 13, 287-303.

IL-17 may contribute to a number of diseases mediated by abnormal immune responses, such as rheumatoid arthritis and air-way inflammation, as well as organ transplant rejection and antitumour immunity. Inhibitors of IL-17 activity are well known in the art, for example an IL-17R:Fc fusion protein was used to demonstrate the role of IL-17 in collagen-induced arthritis (Lubberts et al., J. Immunol. 2001, 167, 1004-1013) and neutralising polyclonal antibodies have been used to reduce peritoneal adhesion formation (Chung et al., 2002, J. Exp. Med., 195, 1471-1478). Neutralising monoclonal antibodies are commercially available (R&D Systems UK).

Multiple sclerosis (MS) is a chronic, inflammatory, demyelinating disease of the central nervous system (CNS), which is believed to result from a coordinated autoimmune attack against myelin antigens. There is considerable clinical and pathological heterogeneity in MS patients and the sequence of events that initiate the disease remain largely unknown. The clinical progression of MS may be largely attributed to three disease processes; inflammation, demyelination and axonal loss/neurodegeneration.

Immune mediated inflammatory lesions within the CNS are thought to result primarily from an infiltration of autoreactive CD4+ lymphocytes (Th1) which recognise myelin proteins presented on MHC class II molecules by antigen presenting cells. This interaction causes stimulation of Th1 cells which release proinflammatory cytokines (mainly TNF-α & IFN-γ) resulting in proliferation of T-cells, activation of B-cells and macrophages, upregulation of adhesion molecules and disruption of the blood-brain barrier. Such events ultimately lead to loss of oligodendrocytes & axons and the formation of a demyelinated plaque. This is the hallmark of MS and consists of a demarcated lesion where myelin sheaths are completely lost and demyelinated axons are embedded in glial scar tissue. Demyelination may also occur as a consequence of specific recognition and opsonization of myelin antigens by autoantibodies. The most important target antigen is suggested to be myelin oligodendrocyte protein (MOG), which is present on the surface of the myelin sheath. Destruction of antibody-opsonized myelin is then accomplished either by complement or activated macrophages. Axonal loss and neurodegeneration subsequent to inflammation are thought to be responsible for the accumulation of irreversible neurological impairment, characteristic of secondary progressive MS.

The clinical features of MS vary from headaches and blurred vision to severe ataxia, blindness and paralysis. MS affects all ages but first symptoms generally occur between 18 and 50 years and disease duration has been estimated at >25 years with a significant proportion of patients dying from causes unrelated to MS. In the majority of patients (~80%) the disease takes a relapsing-remitting (RR-MS) course with exacerbation of symptoms, which is rapid in onset (hours to days) followed by a slower recovery. The frequency and duration of relapses are unpredictable but average 1.5 per year and can be followed by complete recovery. With time, recovery from relapses may not be complete and a gradual worsening of disease occurs. This worsening of disease is independent of relapse rate and is classified as secondary progressive MS (SP-MS), accounting for approximately 10% of MS patients. The remaining 10% of MS patients have a primary progressive (PP-MS) course where disability worsens at a steady rate from onset of the disease.

Currently licensed therapies are the beta-interferons; Interferon beta-1b (Betaseron; Berlex), Interferon beta-1a (Avonex; Biogen, Rebif; Serono) and glatimer acetate (Copaxone; Teva). These agents have been shown to reduce relapse rate during the relapsing-remitting phase of the disease in approximately 30% of patients. There is currently no method available for identifying the responder population before therapy. Intravenous steroids (prednisolone is most commonly used) are used to hasten remission after relapse but do not have long term efficacy. The anti-cancer agent, mitoxantrone (Novantrone), is approved as an immunosuppressant in progressive-relapsing and secondary-progressive patients, but its use and dose is limited by cardiotoxicity. In Europe azathioprine has also been used as an immunosuppressant.

Prescribing decisions seem to be driven by evidence-based medicine and a recent report by the American Association of Neurologists (Goodin D S et al; Neurology 2002 Jan. 22; 58(2):169-78) is a key document. The consensus amongst many neurologists is that early, aggressive therapy with beta-interferons was desirable in increasing the time to first relapse and limiting the overall disease load, although it was recognised that there was no evidence that this approach showed long-term benefit on EDSS score (a measure of disease-related disability). Beta-interferons were seen as sub-optimal therapy and glatirimer acetate as having a different mechanism of action, which may allow it to be used (alone or in combination) in patients that do not respond to interferons. Individualised therapy based on mechanistic (MRI, genetic, neurological) markers of disease was seen as a worthwhile goal, as were therapies with a novel mechanism of action. There is currently no satisfactory diagnostic marker for multiple sclerosis.

There is a clear need for disease modifying therapies. Agents with different mechanisms of action are needed and may allow therapy to be tailored to different stages of the disease. An orally active agent is yet to be licensed in the relapsing-remitting form of the disease and this would represent a clear improvement over current therapy if significant efficacy was associated with the mechanism. Furthermore, there is a clear requirement for therapies that show efficacy in the primary or secondary progressive phases of the disease and have a reasonable side-effect profile.

Whether IL-17 plays any kind of role in the pathogenesis of MS is unknown. Microarray analysis of MS lesions obtained at autopsy have revealed increased transcripts of many different genes encoding inflammatory cytokines, including, IL-17 (Lock et al., 2002, Nature Medicine, 8, 500-508). An increased number of IL-17 expressing mononuclear cells have been detected in blood and cerebrospinal fluid from patients with MS (Matusevicius et al., 1999, Multiple Sclerosis, 5, 101-104) but as the authors point out cytokine mRNA expression is not necessarily identical to cytokine protein production.

Surprisingly we have been able to demonstrate that inhibitors of IL-17 activity are active in an animal model of MS. Specifically we have been able to demonstrate that an anti-IL-17 antibody that inhibits IL-17 activity is active in animal models of MS. Hence, the present invention provides a method for the treatment and/or prophylaxis of MS comprising administering a therapeutically effective amount of an inhibitor of IL-17 activity. The invention also provides the use of an inhibitor of IL-17 activity for the manufacture of a medicament for the treatment and/or prophylaxis of multiple sclerosis.

The term 'IL-17 activity' as used herein refers to the spectrum of activity understood in the art for IL-17 for example, the induction of secretion of IL-6 or IL-8 from fibroblasts by IL-17 (Yao et al., 1995, Journal of Immunology, 155, 5483-5486).

An inhibitor of IL-17 activity according to the present invention is an agent that interferes with the activity of IL-17, in particular the activity of IL-17 in MS. Particularly preferred are agents which interfere with the activity of IL-17 in MS in humans. Inhibitors according to the present invention may partially or completely inhibit IL-17 activity. Inhibitors of use in the present invention include without limitation, inhibitors that are capable of interacting with (e.g. binding to, or recognising) IL-17 or the IL-17 receptor (IL-17 R) or a nucleic acid molecule encoding IL-17 or IL-17R, or are capable of inhibiting the expression of IL-17 or IL-17 R or are capable of inhibiting the interaction between IL-17 and IL-17R. Such inhibitors may be, without limitation, antibodies, nucleic acids (e.g. DNA, RNA, antisense RNA and siRNA), carbohydrates, lipids, proteins, polypeptides, peptides, peptidomimetics, small molecules and other drugs.

Examples of suitable inhibitors include, but are not limited to, a synthetic functional fragment of the IL-17 receptor that binds to IL-17 and interferes with binding to the native IL-17 receptor, an antibody that binds to IL-17 or to the IL-17 receptor and interferes with IL-17 receptor-ligand interaction, an antisense nucleic acid molecule that specifically hybridizes to mRNA encoding IL-17 or the IL-17 receptor or a small molecule or other drug which inhibits the activity of IL-17 or its receptor.

Inhibitors of IL-17 activity are well known in the art as are methods of identifying and producing such inhibitors. Examples include, IL-17R:Fc fusion proteins (Lubberts et al., J. Immunol. 2001, 167, 1004-1013) and neutralising antibodies (Chung et al., 2002, J. Exp. Med., 195, 1471-1478; Ferretti, 2003, Journal of Immunology, 170, 2106-2112). Agents that may be suitable inhibitors can be selected from a wide variety of candidate agents. Examples of candidate agents include but are not limited to, nucleic acids (e.g. DNA and RNA), carbohydrates, lipids, proteins, polypeptides, peptides, peptidomimetics, small molecules and other drugs.

Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is suited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683).

Examples of suitable methods based on the present description for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al, 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, for example, in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

In one example, the inhibitor for use in the present invention may be a nucleic acid. In particular IL-17 or IL-17R nucleic acid molecules may be used as anti-sense molecules, to alter the expression of their respective polypeptides by binding to complementary nucleic acids. IL-17 or IL-17R nucleic acids may be obtained using standard cloning techniques from for example genomic DNA or cDNA or can be synthesised using well known and commercially available techniques. The IL-17 or IL-17R nucleic acids may contain one or more nucleotide substitutions, additions or deletions into the nucleotide sequence of an IL-17 or IL-17R nucleic acid. Standard techniques known to those of skill in the art can be used to introduce mutations, including, for example, site-directed mutagenesis and PCR-mediated mutagenesis. An antisense nucleic acid according to the present invention includes a IL-17 or IL-17R nucleic acid capable of hybridising by virtue of some sequence complementarity to a portion of an RNA (preferably mRNA) encoding the respective polypeptide. The antisense nucleic acid can be complementary to a coding and/or non-coding region of an mRNA encoding such a polypeptide. Most preferably, the antisense nucleic acids result in inhibition of the expression of the IL-17 or IL-17R polypeptide. Thus, the present invention provides a method for the treatment and/or prophylaxis of MS comprising administering a therapeutically effective amount of an inhibitor of IL-17 activity wherein the inhibitor comprises at least eight nucleotides that are antisense to a gene or cDNA encoding a IL-17 or IL-17R polypeptide. The invention also provides the use of nucleic acids comprising at least eight nucleotides that are antisense to a gene or cDNA encoding a IL-17 or IL-17R polypeptide for the manufacture of a medicament for the treatment and/or prophylaxis of MS.

Most preferably, an inhibitor for use in the treatment and/or prophylaxis of MS is an antibody that interacts with (i.e. binds to or recognises) IL-17 or its receptor and inhibits the activity of IL-17. Accordingly, there is provided the use of an antibody that inhibits the activity of IL-17 for the manufacture of a medicament for the treatment and/or prophylaxis of MS. Also provided is a method of treatment and/or prophylaxis of MS in a subject comprising administering to said subject a therapeutically effective amount of an antibody that inhibits the activity of IL-17.

In one example the antibodies selectively interact with IL-17. Selectively interacting with (e.g. recognising or binding to) means that the antibodies have a greater affinity for IL-17 polypeptides than for other polypeptides. Examples of suitable antibodies are those that inhibit the activity of IL-17 by binding to IL-17 in such a manner as to prevent it being biologically active, for example by preventing the binding of IL-17 to its receptor. Accordingly, there is provided by the present invention the use of an anti-IL-17 antibody for the manufacture of a medicament for the treatment and/or prophylaxis of MS. Also provided is a method of treatment and/or prophylaxis of MS in a subject comprising administering to said subject a therapeutically effective amount of an anti-IL-17 antibody.

In another example the antibodies selectively interact with the IL-17 receptor. Selectively interacting with (e.g. recognising or binding to) means that the antibodies have a greater affinity for the IL-17 receptor polypeptide than for other polypeptides. Examples of suitable antibodies are those that inhibit the activity of IL-17 by preventing IL-17 mediated signalling from the receptor, for example by preventing IL-17 from binding to the IL-17 receptor. Accordingly, there is provided by the present invention the use of an anti-IL-17R antibody for the manufacture of a medicament for the treatment and/or prophylaxis of MS. Also provided is a method of treatment and/or prophylaxis of MS in a subject comprising administering to said subject a therapeutically effective amount of an anti-IL-17R antibody.

IL-17 or IL-17 receptor polypeptides or cells expressing said polypeptides can be used to produce antibodies which specifically recognise said polypeptides. The IL-17 and IL-17 R polypeptides may be 'mature' polypeptides or biologically active fragments or derivatives thereof. IL-17 and IL-17 R polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. IL-17 or IL-17R polypeptides may in some instances be part of a larger protein such as a fusion protein for example fused to an affinity tag. Antibodies generated against these polypeptides may be obtained by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986. Many warm-blooded animals, such as rabbits, mice, rats, sheep, chickens, cows or pigs may be immunised. However, mice, rabbits, pigs and rats are generally preferred.

Anti-IL-17 and anti-IL-17 receptor antibodies for use in the present invention include whole antibodies and functionally active fragments or derivatives thereof and may be, but are not limited to, polyclonal, monoclonal, multi-valent, multi-specific, humanized or chimeric antibodies, single chain antibodies, Fab fragments, Fab' and F(ab')$_2$ fragments, fragments produced by a Fab expression library, anti-idiotypic (anti-Id) antibodies, and epitope-binding fragments of any of the above. Antibodies include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule.

Monoclonal antibodies may be prepared by any method known in the art such as the hybridoma technique (Kohler & Milstein, 1975, Nature, 256:495-497), the trioma technique, the human B-cell hybridoma technique (Kozbor et al, 1983, Immunology Today, 4:72) and the EBV-hybridoma technique (Cole et al, Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-7848 and in WO92/02551.

Humanized antibodies are antibody molecules from non-human species having one or more complementarity determining regions (CDRs) from the non-human species and a framework region from a human immunoglobulin molecule (see, e.g. U.S. Pat. No. 5,585,089).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Multivalent antibodies may comprise multiple specificities or may be monospecific (see for example WO 92/22853).

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies to IL-17 or IL-17R polypeptides. Also, transgenic mice, or other organisms, including other mammals, may be used to express humanized antibodies.

Antibody fragments and methods of producing them are well known in the art, see for example Verma et al., 1998, Journal of Immunological Methods, 216, 165-181.

Particular examples of antibody fragments for use in the present invention are Fab' fragments which possess a native or a modified hinge region. A number of modified hinge regions have already been described, for example, in U.S. Pat. No. 5,677,425, WO9915549, and WO9825971 and these are incorporated herein by reference Further examples of particular antibody fragments for use in the present invention include those described in International patent applications PCT/GB2004/002810, PCT/GB2004/002870 and PCT/GB2004/002871 (all filed on 1 Jul. 2004). In particular the modified antibody Fab fragments described in International patent application PCT/GB2004/002810 are preferred. These Fab fragments comprise a heavy and light chain pair, $V_H/C_H1$ and $V_L/C_L$ covalently linked through interchain cysteines in the heavy and light chain constant regions and are characterised in that the heavy chain constant region terminates at the interchain cysteine of $C_H1$. The term 'interchain cysteine' refers to a cysteine in the heavy or light chain constant region that would be disulphide linked to a cysteine in the corresponding heavy or light chain constant region encoded in a naturally occurring germline antibody gene. In particular the interchain cysteines are a cysteine in the constant region of the light chain ($C_L$) and a cysteine in the first constant region of the heavy chain ($C_H1$) that are disulphide linked to each other in naturally occurring antibodies. Examples of such cysteines may typically be found at position 214 of the light chain and position 233 of the heavy chain of human IgG1, position 127 of the heavy chain of human IgM, IgE, IgG2, IgG3, IgG4 and position 128 of the heavy chain of human IgD and IgA2B, as defined by Kabat et al., 1987, in Sequences of Proteins of Immunological Interest, US Department of Health and Human Services, NIH, USA. In murine IgG, interchain cysteines may be found at position 214 of the light chain and position 235 of the heavy chain. It will be appreciated that the exact positions of these cysteines may vary from that of naturally occurring antibodies if any modifications, such as deletions, insertions and/or substitutions have been made to the antibody Fab fragment. These antibody Fab fragments may be prepared by any suitable method known in the art. For example, the antibody Fab fragment may be obtained from any whole antibody, especially a whole monoclonal antibody, using any suitable enzymatic cleavage and/or digestion techniques, for example by treatment with pepsin or papain and c-terminal proteases. Preferably these antibody Fab fragments are prepared by the use of recombinant DNA techniques involving the manipulation and re-expression of DNA encoding antibody variable and constant regions. Standard molecular biology techniques may be used to modify, add or delete further amino acids or domains as desired. Any alterations to the variable or constant regions are still encompassed by the terms 'variable' and 'constant' regions as used herein. Preferably PCR is used to introduce a stop codon immediately following the codon encoding the interchain cysteine of $C_H1$, such that translation of the $C_H1$ domain stops at the interchain cysteine. Methods for designing suitable PCR primers are well known in the art and the sequences of antibody $C_H1$ domains are readily available (Kabat et al., supra). Alternatively stop codons may be introduced using site-directed mutagenesis techniques such as those described in White (Ed.), PCR Protocols: Current Methods and Applications (1993). In one example the constant regions in these fragments are derived from IgG1 and the interchain cysteine of $C_L$ is at position 214 of the light chain and the interchain cysteine of $C_H1$ is at position 233 of the heavy chain. Examples of human and murine constant region sequences for use in these fragments are provided in SEQ ID Nos 1-4 and FIG. 13; human heavy chain constant region $C_H1$ which terminates at the interchain cysteine (SEQ ID NO:1); human light chain constant region (SEQ ID NO:2); murine heavy chain constant region $C_H1$ which terminates at the interchain cysteine (SEQ ID NO:3); murine light chain constant region (SEQ ID NO:4).

If desired an antibody for use in the present invention may be conjugated to one or more effector molecule(s). The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. In one example, anti-IL-17 or anti IL-17 R antibodies can be conjugated to an effector molecule, such as a cytotoxic agent, a radionuclide or drug moiety to modify a given biological response. For example, the therapeutic agent may be a drug moiety which may be a protein or polypeptide possessing a desired biological activity. Such moieties may include, for example and without limitation, a toxin such as abrin, ricin A, pseudomonas exotoxin, or diphtheria toxin, a protein such as tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

In another example the effector molecules may be cytotoxins or cytotoxic agents including any agent that is detrimental to (e.g. kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). In one example, the antibody or fragment thereof is fused via a covalent bond (e.g. a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. Recombinant DNA procedures may be used to create such fusions, for example as described in WO 86/01533 and EP 0392745.

In another example the effector molecule may increase half-life in vivo, and/or decrease immunogenicity and/or enhance the delivery of an antibody across an epithelial barrier to the immune system. Examples of suitable effector molecules include polymers and proteins such as albumin and albumin binding proteins. Examples of suitable polymers include any synthetic or naturally occurring substantially water-soluble, substantially non-antigenic polymer including, for example, optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen. Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol). Preferably the polymer is a polyalkylene oxide such as polyethylene glycol (PEG).

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods. See for example U.S. Pat. No. 5,219,996. Multiple sites can be used to attach two or more PEG molecules. Preferably PEG molecules are covalently linked through a thiol group of at least one cysteine residue located in the antibody fragment. Where a thiol group is used as the point of attachment appropriately activated effector molecules, for example thiol selective derivatives such as maleimides and cysteine derivatives may be used.

Preferably, the antibody is a modified Fab fragment, such as a Fab' which is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. The total amount of PEG attached to the fragment may be varied as desired, but will generally be in an average molecular weight range from 250 to 100,000 Da, preferably from 5,000 to 50,000 Da, more preferably from 10,000 to 40,000 Da and still more preferably from 20,000 to 40,000 Da. The size of PEG may in particular be selected on the basis of the intended use of the product, for example ability to localize to certain tissues such as tumors or extend circulating half-life (for review see Chapman, 2002, Advanced Drug Delivery Reviews, 54, 531-545).

In one embodiment PEG is attached to a cysteine in the hinge region of a Fab'. In one example, a PEG modified Fab' fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab' fragment may therefore be approximately 40,000 Da.

In another preferred embodiment an antibody fragment for use in the present invention is a PEGylated (i.e. has PEG (poly(ethyleneglycol)) covalently attached thereto) Fab fragment as described in International Application Number PCT/GB2004/002810 (filed on 1 Jul. 2004). This PEGylated Fab fragment is a Fab fragment in which the heavy chain terminates at the interchain cysteine of $C_H1$ and the PEG attached to the fragment, preferably PEG-maleimide, is covalently linked to the interchain cysteine of $C_L$ and the interchain cysteine of $C_H1$. Preferably the interchain cysteine of $C_L$ is at position 214 of the light chain and the interchain cysteine of $C_H1$ is at position 233 of the heavy chain. As discussed above the total amount of PEG attached to the fragment may be varied as desired. In one example each polymer attached to the Fab preferably has a molecular weight of approximately 20,000 Da. For example, the molecular weight may be 15,000-25,000 Da, or preferably 18,000-22,000 Da, and even more preferably 19,000-21,000 Da. The total molecular weight of the PEG attached to the antibody is therefore approximately 40,000 Da.

PEG is attached to these fragments by first reducing the interchain disulphide bond between the interchain cysteines of $C_L$ and $C_H1$ and subsequently attaching the PEG to the free thiols. Once PEG is attached to the interchain cysteines there is no interchain disulphide linkage between the heavy and light chain. Suitable reducing agents for reducing the interchain disulphide bond are widely known in the art for example those described in Singh et al., 1995, Methods in Enzymology, 251, 167-73. Particular examples include thiol based reducing agents such as reduced glutathione (GSH), β-mercaptoethanol (β-ME), β-mercaptoethylamine (β-MA) and dithiothreitol (DTT). Other methods include using electrolytic methods, such as the method described in Leach et al., 1965, Div. Protein. Chem., 4, 23-27 and using photoreduction methods, such as the method described in Ellison et al., 2000, Biotechniques, 28 (2), 324-326. Preferably however, the reducing agent is a non-thiol based reducing agent, preferably one of the trialkylphosphine reducing agents (Ruegg U T and Rudinger, J., 1977, Methods in Enzymology, 47, 111-126; Burns J et al., 1991, J. Org. Chem., 56, 2648-2650; Getz et al., 1999, Analytical Biochemistry, 273, 73-80; Han and Han, 1994, Analytical Biochemistry, 220, 5-10; Seitz et al., 1999, Euro. J. Nuclear Medicine, 26, 1265-1273), particular examples of which include tris(2-carboxyethyl)phosphine (TCEP), tris butyl phosphine (TBP), tris-(2-cyanoethyl)phosphine, tris-(3-hydroxypropyl)phosphine (TBP) and tris-(2-hydroxyethyl)phosphine. Most preferred are the reducing agents TCEP and THP. It will be clear to a person skilled in the art that the concentration of reducing agent can be determined empirically, for example, by varying the concentration of reducing agent and measuring the number of free thiols produced. Typically the reducing agent is used in excess over the antibody fragment for example between 2 and 1000 fold molar excess. Preferably the reducing agent is in 2, 3, 4, 5, 10, 100 or 1000 fold excess. In one embodiment the reductant is used at between 2 and 5 mM.

The reduction and PEGylation reactions may generally be performed in a solvent, for example an aqueous buffer solution such as acetate or phosphate, at around neutral pH, for example around pH 4.5 to around pH 8.5, typically pH 4.5 to 8, suitably pH6 to 7. The reactions may generally be performed at any suitable temperature, for example between about 5° C. and about 70° C., for example at room temperature. The solvent may optionally contain a chelating agent such as EDTA, EGTA, CDTA or DTPA. Preferably the solvent contains EDTA at between 1 and 5 mM, preferably 2 mM. Alternatively or in addition the solvent may be a chelating buffer such as citric acid, oxalic acid, folic acid, bicine, tricine, tris or ADA. The PEG will generally be employed in excess concentration relative to the concentration of the antibody fragment. Typically the PEG is in between 2 and 100 fold molar excess, preferably 5, 10 or 50 fold excess.

Where necessary, the desired product containing the desired number of PEG molecules may be separated from any starting materials or other product generated during the production process by conventional means, for example by chromatography techniques such as ion exchange, size exclusion, protein A, G or L affinity chromatography or hydrophobic interaction chromatography.

To identify inhibitors of IL-17 activity a number of different approaches may be taken by those skilled in the art. In one example inhibitors are identified by first identifying agents that interact with IL-17 or IL-17R and subsequently testing those agents to identify those that inhibit IL-17 activity. In one such example the agent is an antibody.

Agents that interact with IL-17 or IL-17R may be identified using any suitable method, for example by using a cell-free or cell-based assay system where the IL-17 or IL-17R polypeptide is contacted with a candidate agent and the ability of the candidate agent to interact with the polypeptide is determined. Preferably, the ability of a candidate agent to interact with a IL-17 or IL-17R polypeptide is compared to a reference range or control. If desired, this assay may be used to screen a plurality (e.g. a library) of candidate agents using a plurality of IL-17 or IL-17R polypeptide samples. In one example of a cell free assay, a first and second sample comprising native or recombinant IL-17 or IL-17R polypeptide are contacted with a candidate agent or a control agent and the ability of the candidate agent to interact with the polypeptide is determined by comparing the difference in interaction between the candidate agent and control agent. Preferably, the polypeptide is first immobilized, by, for example, contacting the polypeptide with an immobilized antibody which specifically recognizes and binds it, or by contacting a purified preparation of polypeptide with a surface designed to bind proteins. The polypeptide may be partially or completely purified (e.g. partially or completely free of other polypeptides) or part of a cell lysate. Further, the polypeptide may be a fusion protein comprising the IL-17 or IL-17R polypeptide or a biologically active portion thereof and a domain such as glutathionine-S-transferase or the Fc region of IgG1. Alternatively, the polypeptide can be biotinylated using techniques well known to those of skill in the art (e.g. biotinylation kit, Pierce Chemicals; Rockford, Ill.). The ability of the candidate agent to interact with the polypeptide can be determined by methods known to those of skill in the art for example, ELISA, BIAcore™, Flow cytometry or fluorescent microvolume assay technology (FMAT). In another example where a cell-based assay is used, a population of cells expressing IL-17 or IL-17 R is contacted with a candidate agent and the ability of the candidate agent to interact with the polypeptide is determined. Preferably, the ability of a candidate agent to interact with IL-17 or IL-17 R is compared to a reference range or control. The cell, for example, can be of eukaryotic origin (e.g. yeast or mammalian) and can express the IL-17 or IL-17 R polypeptide endogenously or be genetically engineered to express the polypeptide. In some instances, the IL-17 or IL-17R polypeptide or the candidate agent is labelled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between a polypeptide and a candidate agent. Alternative methods such as ELISA, flow cytometry and FMAT may also be used.

Agents which inhibit IL-17 activity may be identified by any suitable method, for example by:

(i) comparing the activity of IL-17 in the presence of a candidate agent with the activity of said polypeptide in the absence of the candidate agent or in the presence of a control agent; and (ii) determining whether the candidate agent inhibits activity of IL-17.

Such assays can be used to screen candidate agents, in clinical monitoring or in drug development.

As described above, agents may be pre-screened where appropriate to identify agents (e.g. an antibody) that interact with IL-17 or IL-17R prior to screening those agents which bind for their ability to inhibit IL-17 activity.

In one example a cell-based assay system is used to identify agents capable of inhibiting the activity of IL-17. In one particular example the assay used to identify inhibitors of IL-17 activity is the standard IL-6 release assay from fibroblasts (Yao et al., 1995, Journal of Immunology, 155, 5483-5486). Potential inhibitors are added to the assay and IL-6 release determined by ELISA. Inhibition is therefore measured as a reduction in IL-6 release compared to controls.

In another example inhibitors of IL-17 may down-regulate the expression of the IL-17 or IL-17R polypeptide, for example antisense inhibitors. Such inhibitors may be identified by any method known in the art. In one example such inhibitors are identified in a cell-based assay system. Accordingly, a population of cells expressing a IL-17 or IL-17R polypeptide or nucleic acid are contacted with a candidate agent and the ability of the candidate agent to alter expression of the IL-17 or IL-17R polypeptide or nucleic acid is determined by comparison to a reference range or control. In one example, populations of cells expressing a IL-17 or IL-17R polypeptide are contacted with a candidate agent or a control agent and the ability of the candidate agent to alter the expression of the IL-17 or IL-17R polypeptides or nucleic acids is determined by comparing the difference in the level of expression of the IL-17 or IL-17R polypeptides or nucleic acids between the treated and control populations of cells. If desired, this assay may be used to screen a plurality (e.g. a library) of candidate agents. The cell, for example, can be of eukaryotic origin (e.g. yeast or mammalian) and can express an IL-17 or IL-17R polypeptide endogenously or be genetically engineered to express a IL-17 or IL-17R polypeptide. The ability of the candidate agents to alter the expression of a said polypeptides or nucleic acids can be determined by methods known to those of skill in the art, for example and without limitation, by flow cytometry, radiolabelling, a scintillation assay, immunoprecipitation, Western blot analysis, Northern blot analysis or RT-PCR.

Agents that inhibit the activity of IL-17 may be identified or further tested, for example to determine therapeutically effective amounts in one or more animal models. Examples of suitable animals include, but are not limited to, mice, rats, rabbits, monkeys, guinea pigs, dogs and cats. Preferably, the animal used represents a model of MS.

In one example where the agent inhibits the expression of IL-17 or IL-17R, a first and second group of mammals are administered with a candidate agent or a control agent and the ability of the candidate agent to inhibit the expression of IL-17 or IL-17R polypeptide or nucleic acid is determined by comparing the difference in the level of expression between the first and second group of mammals. Where desired, the expression levels of the IL-17 or IL-17R polypeptides or nucleic acid in the first and second groups of mammals can be compared to the level of IL-17 or IL-17R polypeptide or nucleic acid in a control group of mammals. The candidate agent or a control agent can be administered by means known in the art (e.g. orally, rectally or parenterally such as intraperitoneally or intravenously). Changes in the expression of a polypeptide or nucleic acid can be assessed by the methods outlined above.

In another example, the inhibition of IL-17 activity can be determined by monitoring an amelioration or improvement in disease symptoms, a delayed onset or slow progression of the disease, for example but without limitation, a reduction in paralysis. Techniques known to physicians familiar with MS can be used to determine whether a candidate agent has altered one or more symptoms associated with the disease.

A number of different models of MS are known in the art ('t Hart and Amor 2003, Current Opinion in Neurology 16:375-83). In particular, experimental autoimmune encephalomyelitis (EAE) in ABH mice is considered to be a relevant model for MS in humans (Baker et al., 1990. Journal of Neuroimmunology, 28:261-270). Both acute and relapsing-remitting models have been developed.

As discussed herein, inhibitors of IL-17 activity can be used in the treatment and/or prophylaxis of MS. For such use the agents will generally be administered in the form of a pharmaceutical composition.

Also provided is a pharmaceutical composition comprising an inhibitor of IL-17 activity and a pharmaceutically acceptable carrier.

The term 'treatment' includes either therapeutic or prophylactic therapy. When a reference is made herein to a method of treating or preventing a disease or condition using a particular inhibitor or combination of inhibitors, it is to be understood that such a reference is intended to include the use of that inhibitor or combination of inhibitors for the manufacture of a medicament for the treatment and/or prophylaxis of MS.

The composition will usually be supplied as part of a sterile, pharmaceutical composition that will normally include a pharmaceutically acceptable carrier. This composition may be in any suitable form (depending upon the desired method of administering it to a patient).

The inhibitors of use in the invention are preferably administered to a subject by a variety of other routes such as orally, transdermally, subcutaneously, intranasally, intravenously, intramuscularly, intrathecally and intracerebroventricularly. The most suitable route for administration in any given case will depend on the particular inhibitor, the subject, and the nature and severity of the disease and the physical condition of the subject.

The inhibitors of use in the invention may be administered in combination, e.g. simultaneously, sequentially or separately, with one or more other therapeutically active compounds, which may be for example other anti-MS therapies or anti-cancer therapies.

Pharmaceutical compositions may be conveniently presented in unit dose forms containing a predetermined amount of an active agent of the invention per dose. Such a unit may contain for example but without limitation, 750 mg/kg to 0.1 mg/kg depending on the condition being treated, the route of administration and the age, weight and condition of the subject.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents as known in the art.

In the case of oral solid preparations such as powders, capsules and tablets, carriers such as starches, sugars, microcrystalline cellulose, granulating agents, lubricants, binders, disintegrating agents, and the like may be included. Because of their ease of administration, tablets and capsules represent the most advantageous oral dosage unit form in which case solid pharmaceutical carriers are generally employed. In addition to the common dosage forms set out above, active agents of the invention may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the active agent, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active agent with the carrier, which constitutes one or more necessary ingredients. In general, the compositions are prepared by uniformly and intimately admixing the active agent with liquid carriers or finely divided solid carriers or both, and then, if necessary, shaping the product into the desired presentation. For example, a tablet may be prepared by compression or moulding, optionally with one or more accessory ingredients.

Pharmaceutical compositions suitable for parenteral administration may be prepared as solutions or suspensions of the active agents of the invention in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. No. 5,399, 163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollients in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base. Alternatively, the active agent may be formulated in a cream with an oil-in-water cream base or a water-in-oil base.

Pharmaceutical compositions adapted for topical administration in the mouth include lozenges, pastilles and mouth washes.

Pharmaceutical compositions adapted for topical administration to the eye include eye drops wherein the active agent is dissolved or suspended in a suitable carrier, especially an aqueous solvent. They also include topical ointments or creams as above.

Pharmaceutical compositions suitable for rectal administration wherein the carrier is a solid are most preferably presented as unit dose suppositories. Suitable carriers include cocoa butter or other glyceride or materials commonly used in the art, and the suppositories may be conveniently formed by admixture of the combination with the softened or melted carrier(s) followed by chilling and shaping moulds. They may also be administered as enemas.

The dosage to be administered of an inhibitor of IL-17 activity will vary according to the particular inhibitor, the type of MS, the subject, and the nature and severity of the disease and the physical condition of the subject, and the selected route of administration; the appropriate dosage can be readily determined by a person skilled in the art. For the treatment and/or prophylaxis of MS in humans and animals pharmaceutical compositions comprising antibodies can be administered to patients (e.g., human subjects) at therapeutically or prophylactically effective dosages (e.g. dosages which result in inhibition of MS and/or relief of MS symptoms) using any suitable route of administration, such as injection and other routes of administration known in the art for clinical products, such as antibody-based clinical products.

The compositions may contain from 0.1% by weight, preferably from 10-60%, or more, by weight, of the inhibitor of the invention, depending on the method of administration.

It will be recognized by one of skill in the art that the optimal quantity and spacing of individual dosages of an inhibitor of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

In another example, where the inhibitor is a nucleic acid this may be administered via gene therapy (see for example Hoshida, T. et al., 2002, Pancreas, 25:111-121; Ikuno, Y. 2002, Invest. Opthalmol. Vis. Sci. 2002 43:2406-2411; Bollard, C., 2002, Blood 99:3179-3187; Lee E., 2001, Mol. Med. 7:773-782). Gene therapy refers to administration to a subject of an expressed or expressible nucleic acid. In one example this is either the IL-17 or the IL-17R nucleic acid or portions thereof. Any of the methods for gene therapy available in the art can be used according to the present invention.

Delivery of the therapeutic nucleic acid into a patient can be direct in vivo gene therapy (i.e. the patient is directly exposed to the nucleic acid or nucleic acid-containing vector) or indirect ex vivo gene therapy (i.e. cells are first transformed with the nucleic acid in vitro and then transplanted into the patient).

For example for in vivo gene therapy, an expression vector containing the IL-17 or IL-17R nucleic acid may be administered in such a manner that it becomes intracellular, i.e. by infection using a defective or attenuated retroviral or other viral vectors as described, for example, in U.S. Pat. No. 4,980,286 or by Robbins et al., 1998, Pharmacol. Ther. 80:35-47.

The various retroviral vectors that are known in the art are such as those described in Miller et al. (1993, Meth. Enzymol. 217:581-599) which have been modified to delete those retroviral sequences which are not required for packaging of the viral genome and subsequent integration into host cell DNA. Also adenoviral vectors can be used which are advantageous due to their ability to infect non-dividing cells and such high-capacity adenoviral vectors are described in Kochanek (1999, Human Gene Therapy, 10:2451-2459). Chimeric viral vectors that can be used are those described by Reynolds et al. (1999, Molecular Medicine Today, 1:25-31). Hybrid vectors can also be used and are described by Jacoby et al. (1997, Gene Therapy, 4:1282-1283).

Direct injection of naked DNA or through the use of microparticle bombardment (e.g. Gene Gun®; Biolistic, Dupont) or by coating it with lipids can also be used in gene therapy. Cell-surface receptors/transfecting compounds or through encapsulation in liposomes, microparticles or microcapsules or by administering the nucleic acid in linkage to a peptide which is known to enter the nucleus or by administering it in linkage to a ligand predisposed to receptor-mediated endocytosis (See Wu & Wu, 1987, J. Biol. Chem., 262:4429-4432) can be used to target cell types which specifically express the receptors of interest.

In ex vivo gene therapy, a gene is transferred into cells in vitro using tissue culture and the cells are delivered to the patient by various methods such as injecting subcutaneously, application of the cells into a skin graft and the intravenous injection of recombinant blood cells such as haematopoietic stem or progenitor cells.

Cells into which a IL-17 or IL-17R nucleic acid can be introduced for the purposes of gene therapy include, for example, epithelial cells, endothelial cells, keratinocytes, fibroblasts, muscle cells, hepatocytes and blood cells. The blood cells that can be used include, for example, T-lymphocytes, B-lymphocytes, monocytes, macrophages, neutrophils, eosinophils, megakaryotcytes, granulocytes, haematopoietic cells or progenitor cells, and the like.

In a one aspect, the pharmaceutical composition of the present invention comprises an IL-17 or IL-17R nucleic acid, said nucleic acid being part of an expression vector that expresses an IL-17 or IL-17R polypeptide or chimeric protein thereof in a suitable host. In particular, such a nucleic acid has a promoter operably linked to the polypeptide coding region, said promoter being inducible or constitutive (and, optionally, tissue-specific).

The invention will now be described with reference to the following examples, which are merely illustrative and should not in any way be construed as limiting the scope of the present invention.

FIGURES

FIG. 1. Effect of Ab#13mIgG1 on clinical disease when dosed from day −1 through the acute phase (black arrowheads, days −1, 6, 13, 20). Average clinical score (+/−sd) plotted against day of disease induction (a) and average change in weight from day 0 (b).

Figure 2:
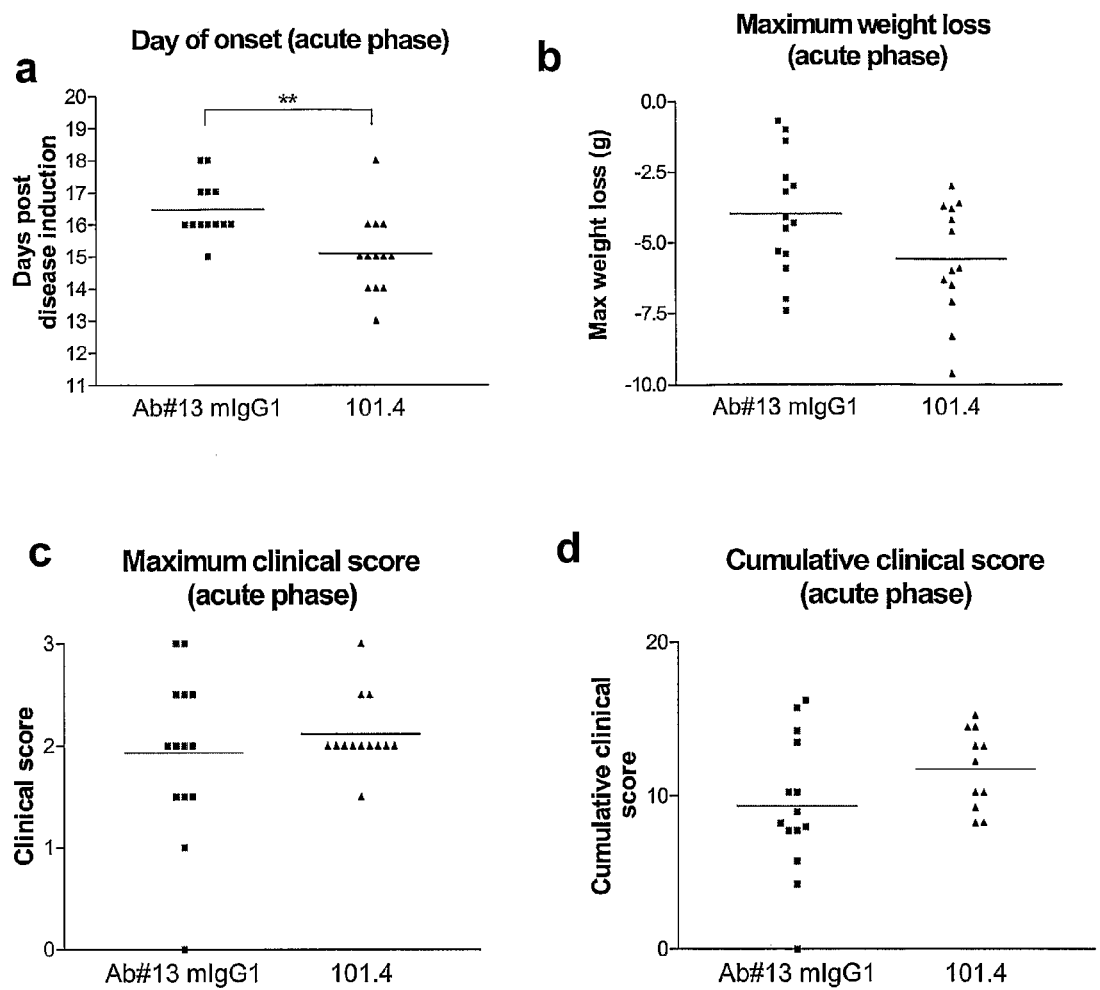

FIG. 2. Analysis of the acute phase of disease following dosing of Ab#13mIgG1 through the acute phase.

Figure 3:
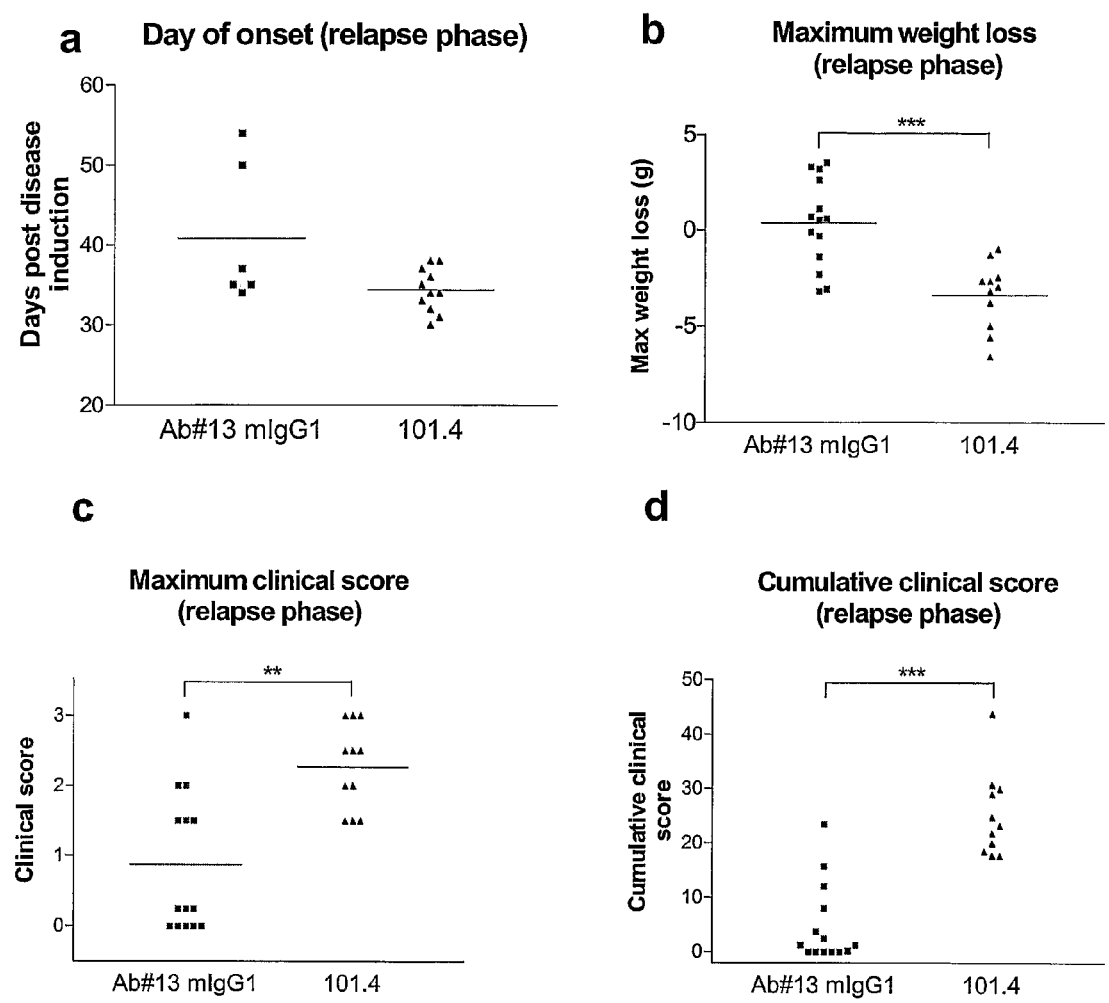

FIG. 3. Analysis of the relapse phase of disease following dosing of Ab#13mIgG1 through the acute phase.

Figure 4:
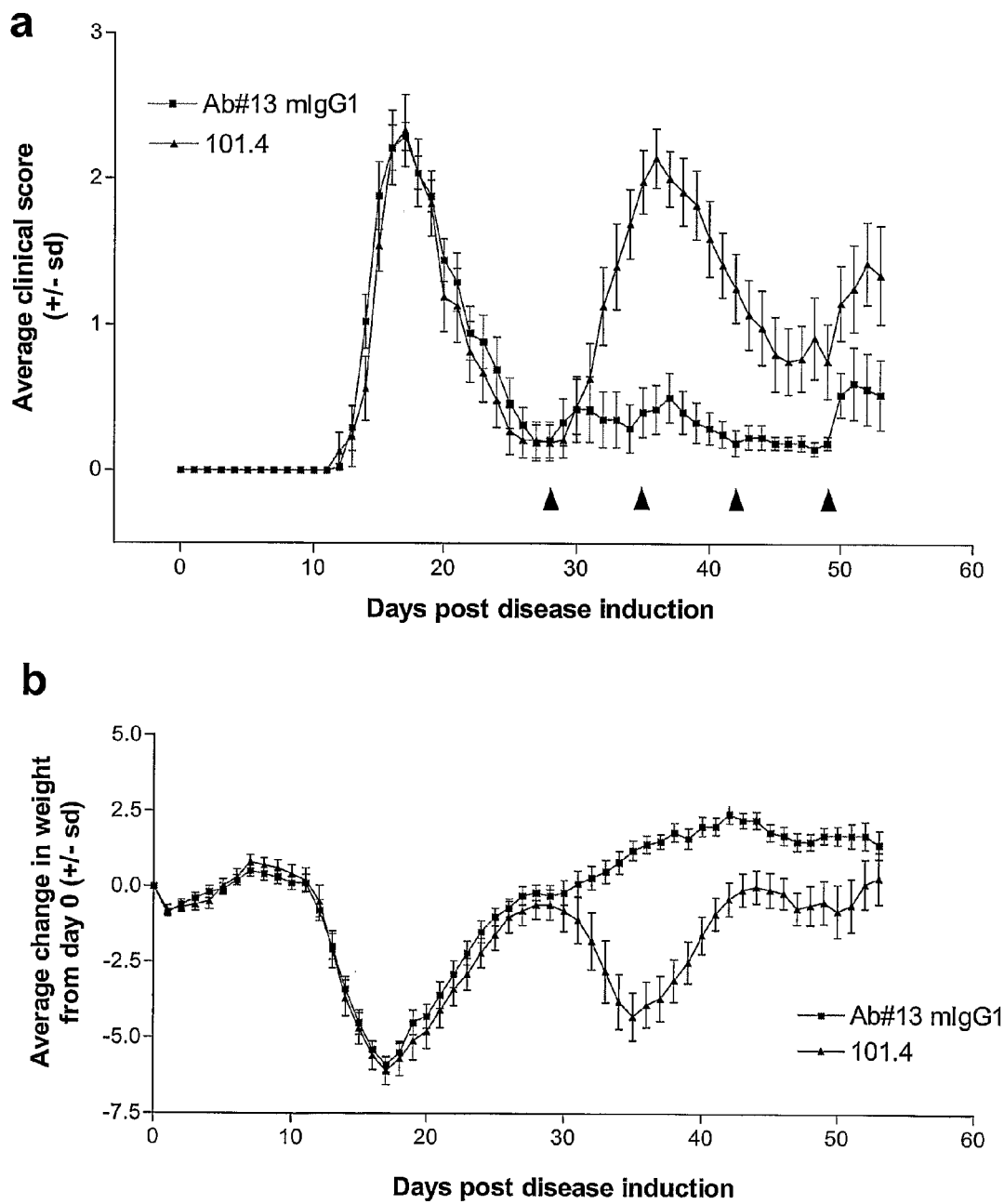

FIG. 4. Effect of Ab#13mIgG1 on clinical disease when dosed through the relapse phase (days 28, 35, 42 and 49, black arrowheads). Average clinical score (+/−sd) versus day of disease induction (a) and average change in weight from day 0 (b).

Figure 5:
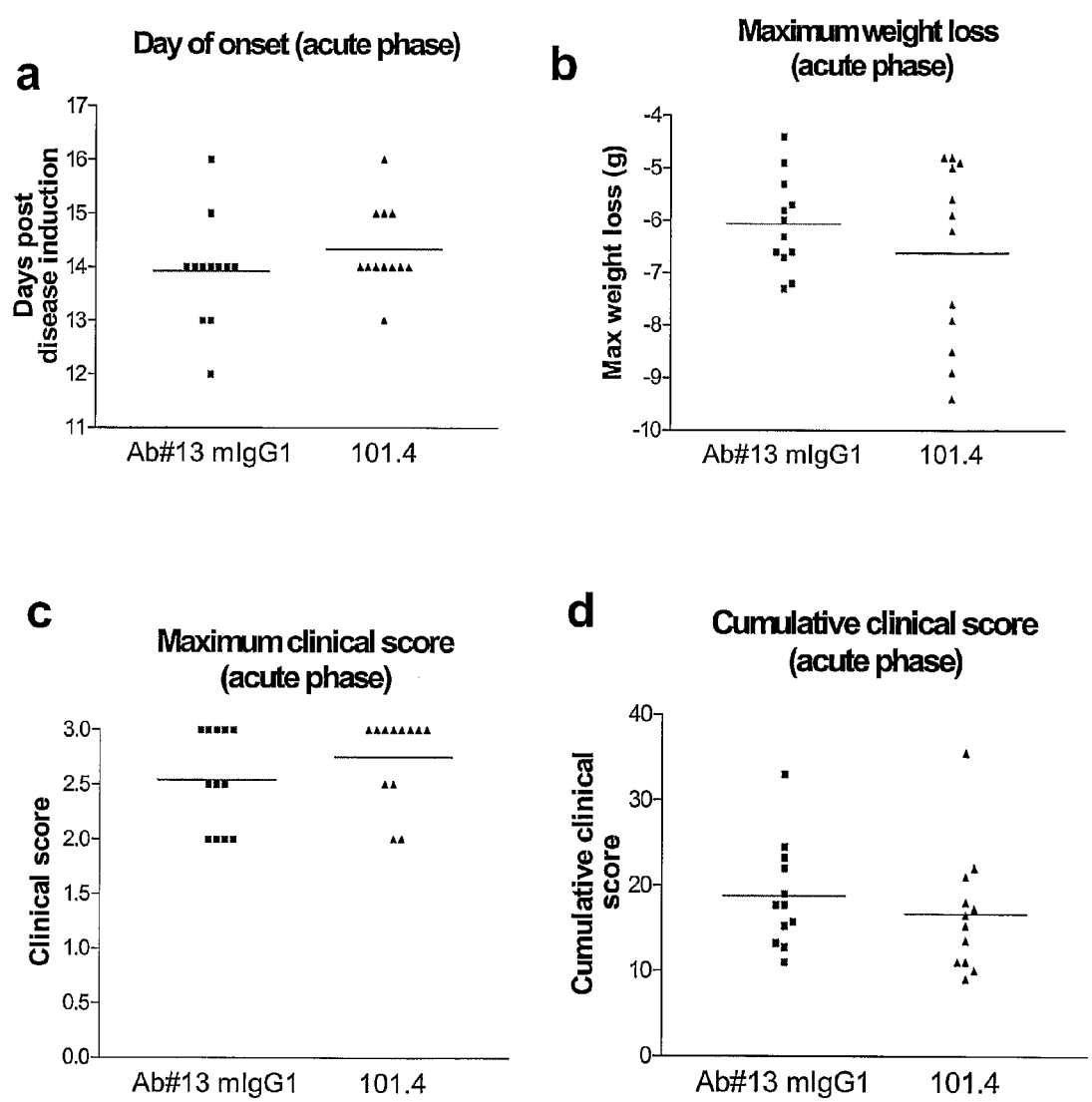

FIG. 5. Analysis of the acute phase of disease following dosing of Ab#13mIgG1 through the relapse phase.

Figure 6:
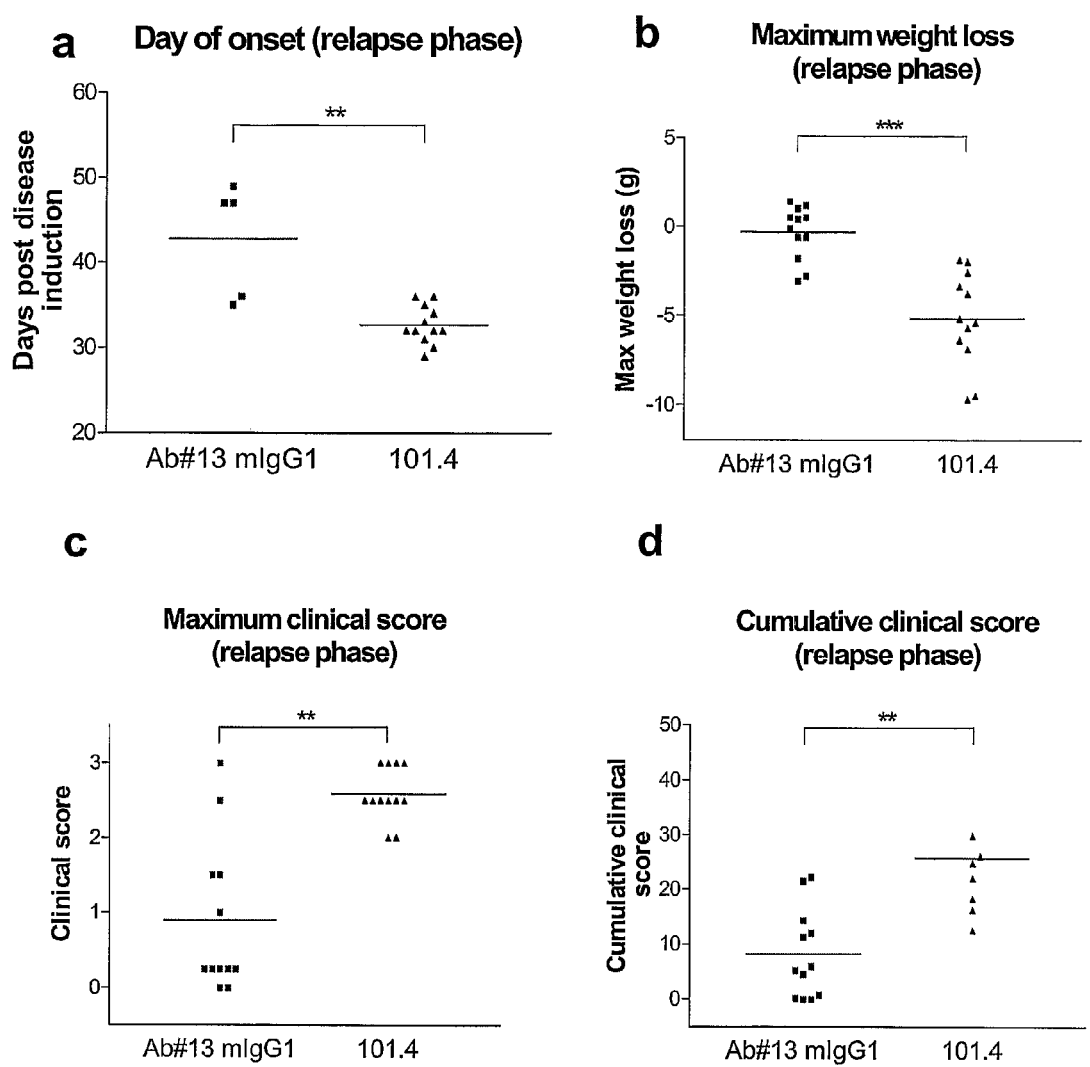

FIG. 6. Analysis of the relapse phase of disease following dosing of Ab#13mIgG1 through the relapse phase.

Figure 7:
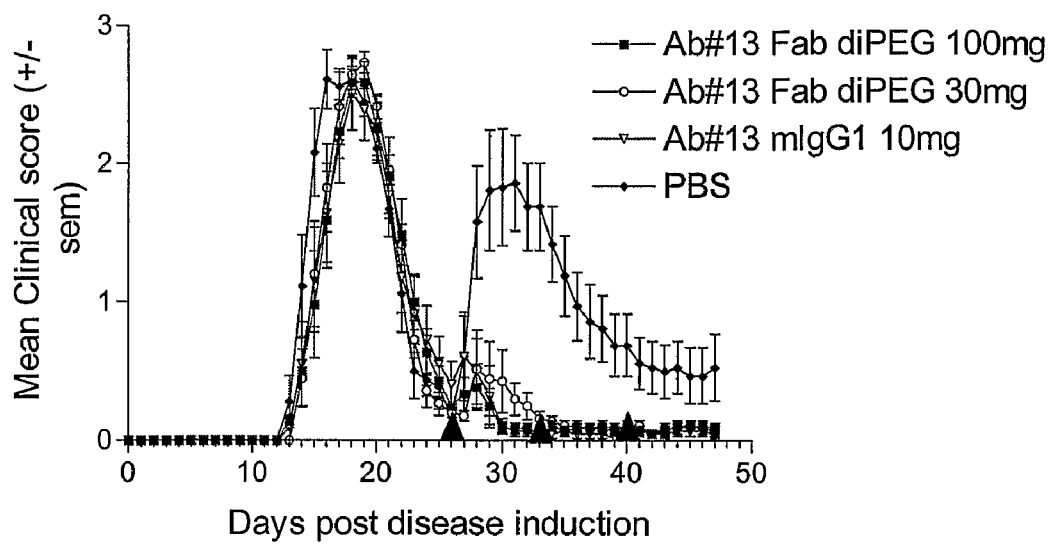
Figure 7:
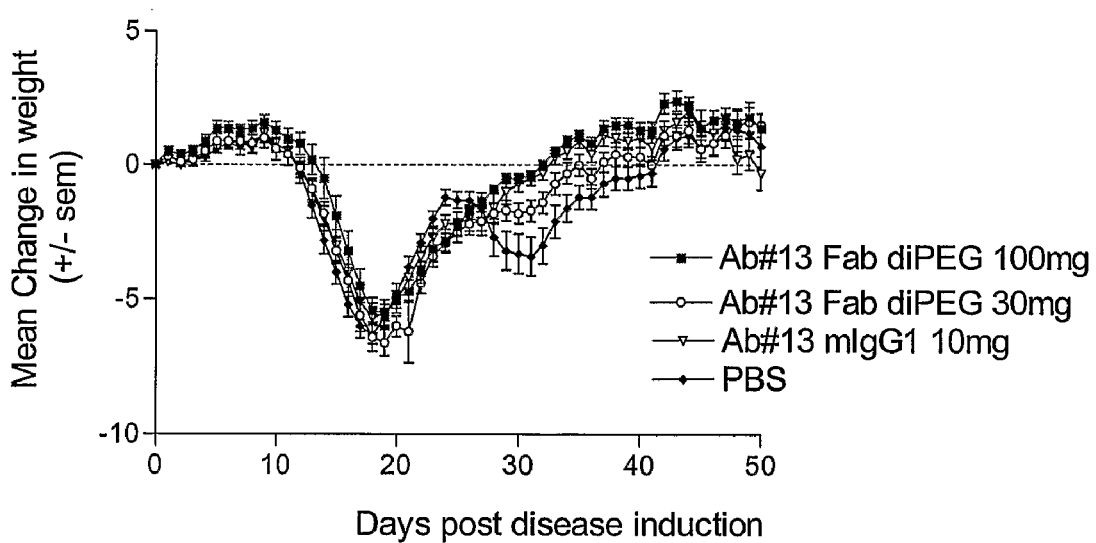

FIG. 7. Effect of Ab#13 Fab-di-PEG and Ab#13 mIgG1 on clinical disease when dosed through the relapse phase (black arrowheads represent dosing days). Average clinical score (+/−sd) plotted against day of disease induction (a) and average change in weight from day 0 (b).

Figure 8:
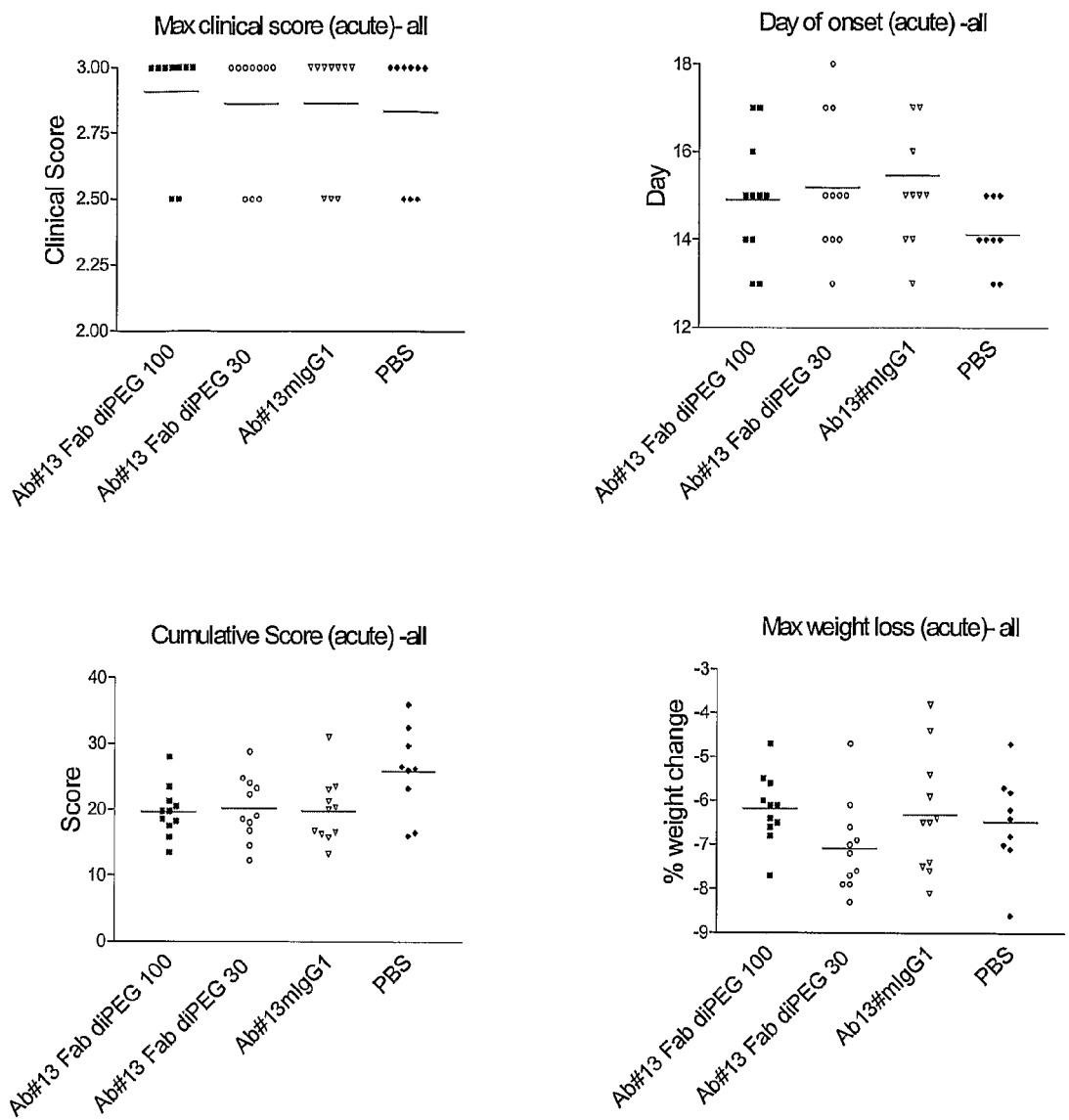

FIG. 8. Analysis of acute phase prior to dosing with Ab#13 Fab-di-PEG and Ab#13 mIgG1.

Figure 9:
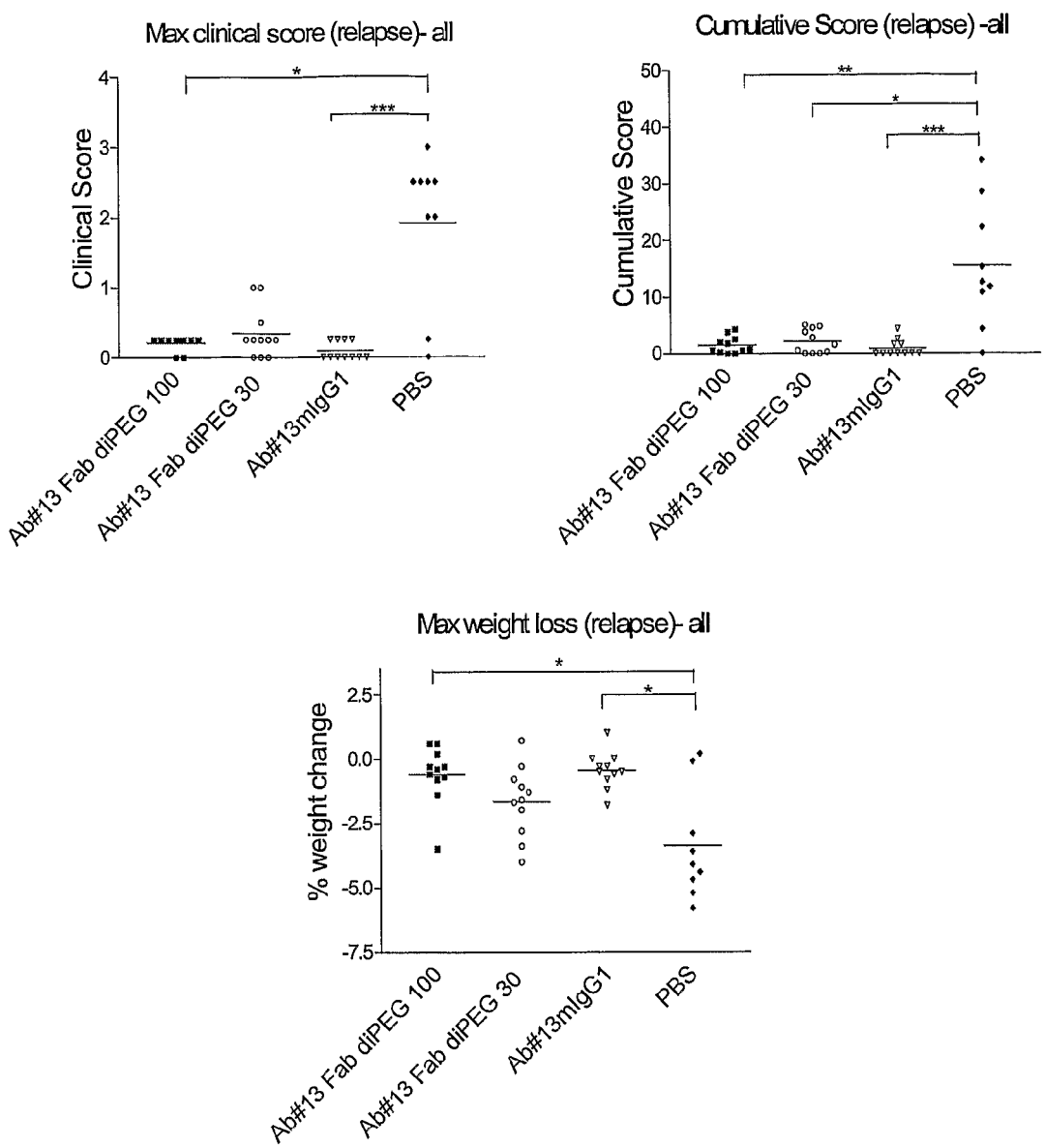

FIG. 9. Analysis of relapse phase following dosing with Ab#13 Fab-di-PEG and Ab#13 mIgG1 during remission.

Figure 10:
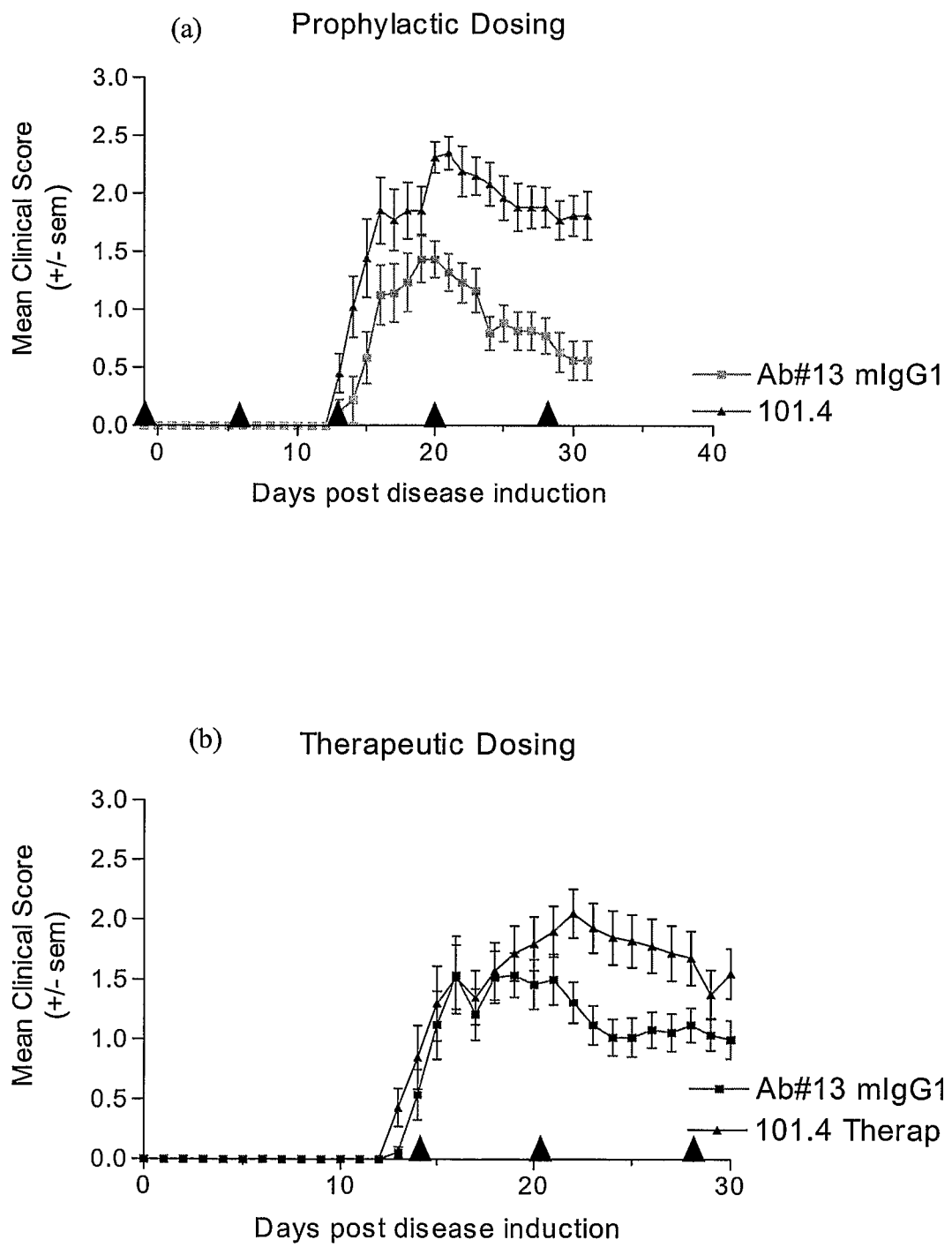

FIG. 10. Effect of Ab#13mIgG1 on clinical disease when dosed from day −1 (black arrowheads represent dosing days, prophylactically (a) and therapeutically (b).

Figure 11:
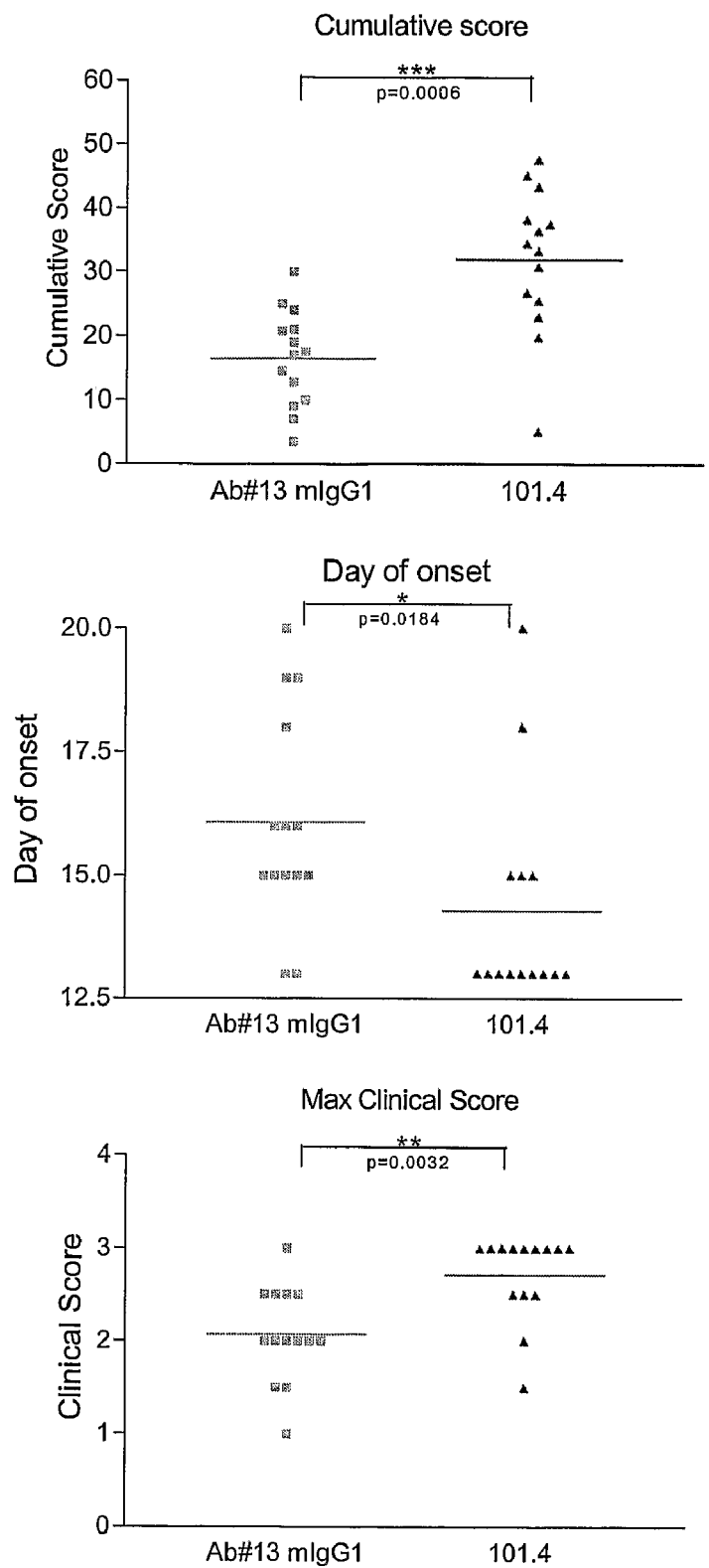

FIG. 11. Analysis of prohylactic dosing regime.

Figure 12:
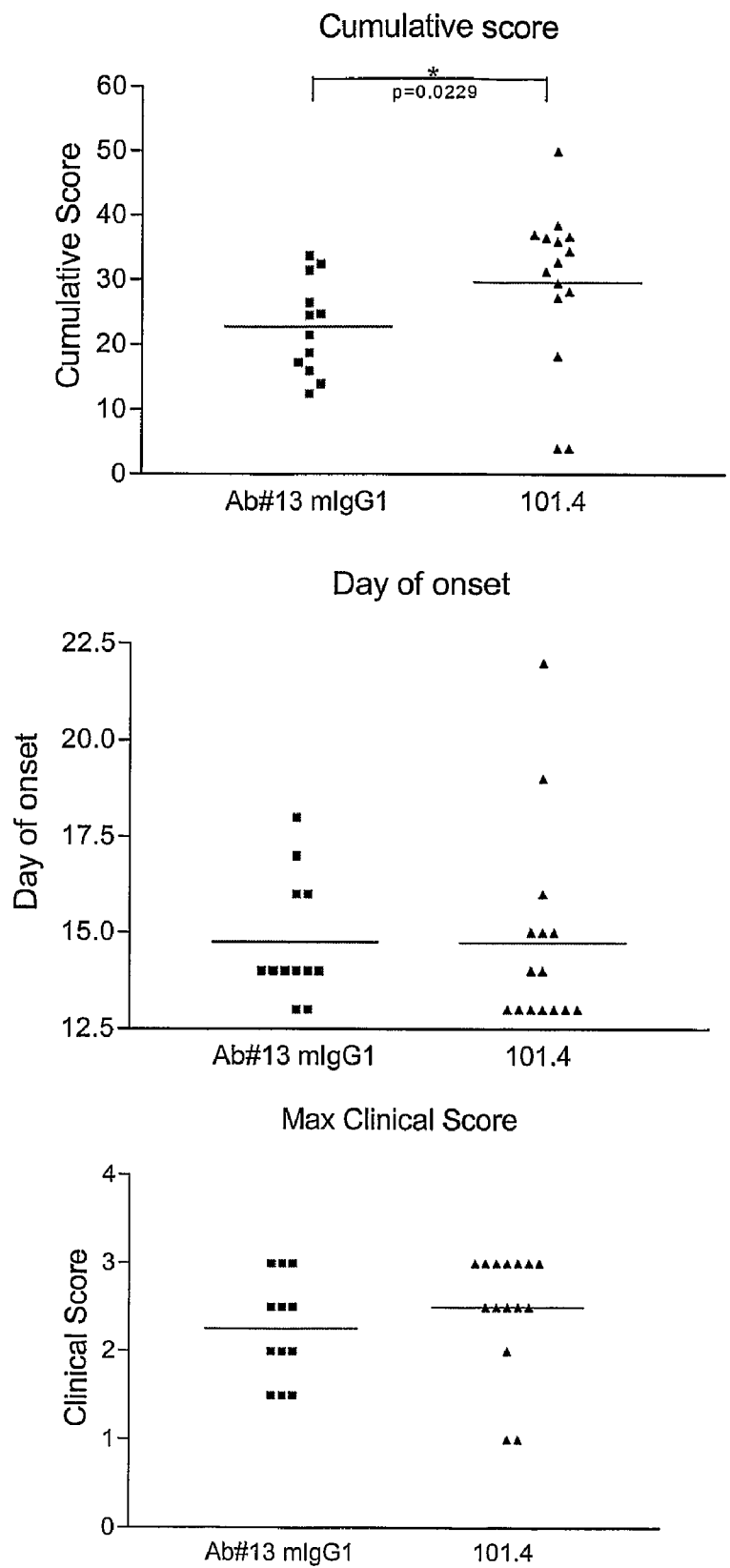

FIG. 12. Analysis of therapeutic dosing regime.

FIG. 13. Human and murine constant regions.

EXAMPLES

Example 1

Isolation of an Anti-IL-17 Antibody

Rabbits were immunised three times with human IL-17 and then twice with mouse IL-17. Using a haemolytic plaque assay with biotinylated sheep red blood cells coated with murine IL-17 via streptavidin, 9 antibody genes were isolated using the methods described by Babcook et al., 1996, Proc. Natl. Acad. Sci, 93, 7843-7848 and in WO92/02551. The antibody genes were expressed in CHO cells and the recombinant antibodies screened for their ability to neutralise murine IL-17 in a bioassay using mouse 3T3-NIH cells (Yao et al., 1995, Immunity, 3:811-821). All the antibodies in the panel neutralised murine IL-17 in this assay and one antibody, m170013 (Ab#13) was selected for in vivo testing. For testing the efficacy of the antibody in EAE, a chimeric IgG (Ab#13 mIgG1) was produced using the rabbit variable region from antibody ml 70013 and mouse constant regions.

Example 2

Effect of Ab#13 mIgG1 on the Symptoms of EAE

The MS model, experimental autoimmune encephalomyelitis (EAE), was used essentially as described by Baker et al., 1990. Journal of Neuroimmunology, 28:261-270. Female ABH mice 8-10 weeks of age (Harlan) were immunised with mouse spinal cord homogenate (SCH, 3.33 mg/ml) in complete freund's adjuvant by subcutaneous immunisation in either flank (150 μl/site) on days 0 and 7.

i) Dosing Over the Acute Phase

Two groups were dosed with antibody at 10 mg/kg, sc on days −1, 6, 13 and 20. One group (n=14) was dosed with Ab#13 mIgG1 the other (n=113) with 101.4 (isotype control).

ii) Dosing Over the Relapsing Phase

A total of 30 mice were followed through the acute phase of disease and on day 27 analysis of the acute phase of disease was performed to select two groups with similar disease profiles in the acute phase (day of onset, peak disease score, cumulative clinical score and weight loss). Two groups of 12 mice were selected for dosing with antibody at 10 mg/kg, sc on days 28, 35, 42 and 49. One group was dosed with Ab#13 mIgG1) the other with 101.4 (isotype control).

Weights and clinical scores were recorded daily by an assessor blinded to treatment and terminal EDTA-Plasma collected.

Clinical Score Scale

| 0 | Normal |
|---|---|
| 0.25 | Tail dragging |
| 0.5 | Partial tail paralysis |
| 1 | Complete tail paralysis |
| 2 | Incomplete hind limb paralysis |
| 3 | Complete hind paralysis/incontinence |
| 4 | Front limb paralysis/loss of righting reflex |

Statistics

Pairwise comparisons of clinical scores and day of onset were performed using Mann-Whitney U test, analysis of incidence was performed with Fishers exact test, analysis of maximum weight loss was performed using Students' T test.

Results i) Dosing during acute phase: A significant delay in the onset of the acute phase and a reduced severity and incidence of first relapse was observed (FIGS. 1, 2 and 3). FIG. 2 shows that Ab#13 mIgG1 dosed through the acute phase had no effect on the incidence of disease in the acute phase (Ab#13 mIgG1, 13/14 with disease vs 13/13 for isotype control, 101.4). The only statistically significant effect was a delay in the onset of the acute phase of disease FIG. 2 a, p=0.0039, Mann-Whitney U test. No effects were seen on weight loss (b), maximum clinical score (c) or cumulative clinical score (d) in the acute phase. FIG. 3 shows that Ab#13 mIgG1 dosed through the acute phase caused a significant reduction in the incidence of the relapse phase of disease (Ab#13 mIgG1, 6/14 with disease vs 11/11 for isotype control, 101.4, p=0.0029, Fishers exact test). There was no statistically significant delay in the onset of the relapse phase of disease for those animals which entered relapse (a). A significant reduction in weight loss (b, p=0.0001, Student's T test), maximum clinical score (c, p=0.0028, Mann-Whitney U test)) and cumulative clinical score (d, p=0.0001, Mann-Witney U test) were observed during the relapse phase.

ii) Dosing through the relapsing phase: A reduced incidence, delayed onset and reduced severity of the relapse phase was observed (see FIGS. 4, 5 and 6). FIG. 5 shows that the dose groups selected to have a similar acute phase profile, showed no significant differences in any of the parameters analysed. FIG. 6 shows that Ab#13 mIgG1 dosed through the relapse phase caused a significant reduction in the incidence of the relapse phase of disease (Ab#13 mIgG1, 5/12 with disease vs 12/12 for isotype control, 101.4, p=0.0046, Fishers exact test). There was also a statistically significant delay in the onset of the relapse phase of disease for those animals which entered relapse (a, p=0.0061). A significant reduction in weight loss (b, p<0.0001, Student's T test), maximum clinical score (c, p=0.0011, Mann-Whitney U test)) and cumulative clinical score (d, p=0.0023, Mann-Whitney U test) were also observed during the relapse phase.

Summary

Ab#13 mIgG1 antibody was dosed in separate experiments over the acute phase of disease (prophylactic dosing) and over the relapse phase (therapeutic dosing). Effects were most pronounced on relapse with a significant reduction in the incidence and severity of the relapse phase for both dosing regimes.

Example 3

Effect of Ab#13 Fab-Di-PEG on the Symptoms of EAE

A Fab fragment, termed Ab#13 Fab-Di-PEG was produced essentially as described in International Patent Application PCT/GB2004/002810 (filed on 1 Jul. 2004). The Fab consisted of the rabbit variable regions of antibody 13 from example 1 and mouse IgG1 constant regions. In contrast to other Fab fragments, the heavy chain constant region of this Fab terminates at the interchain cysteine of $C_H1$. PCR primers were designed based on the murine IgG1 CH1 region and PCR mutagenesis used to insert a stop codon immediately following the interchain cysteine of $C_H1$. The mouse constant regions are shown in FIG. 13 and in SEQ ID Nos 3 (heavy chain) and 4 (light chain). PCR mutagenesis was also used to replace the cysteine at position 80 of the rabbit light chain variable region with alanine.

```
Murine CH1
                                           (SEQ ID NO:3)
KTTPPSVYPLAPGSAAQTNSMVTLGCLVKGYFPEPVTVTWNSGSLSSGVH
TFPAVLQSDLYTLSSSVTVPSSTWPSETVTCNVAHPASSTKVDKKIVPRD
C*

Murine Kappa
                                           (SEQ ID NO:4)
DAAPTVSIFPPSSEQLTSGGASVVCFLNNFYPKDINVKWKIDGSERQNGV
LNSWTDQDSKDSTYSMSSTLTLTKDEYERHNSYTCEATHKTSTSPIVKSF
NRGEC*
```

The Fab fragments were produced in *E. coli* strain W3110 and purified using standard methods (Humphreys et al., 2002, Protein Expression and Purification, 26, 309-320).

2×20 kDa PEG was attached to the Fab fragment by attaching a linear 20 kDa PEG to each of the interchain cysteines (underlined in the sequences above). Reductions and PEGylations were performed in 50 mM Tris.HCl 5 mM EDTA pH 7.14 with Fab at 20.06 mg/ml. The Fab was reduced at room temperature (~24° C.) for 30 minutes using 10 mM tris(2-carboxyethyl)phosphine (TCEP) (final). The Fab was desalted on a PD-10 column (Pharmacia) and then mixed with 4 fold molar excess of linear 20 kDa PEG-maleimide over Fab. The 20 kDa PEG was from Nippon Oils and Fats (NOF). PEGylated Fab was separated from unPEGylated Fab by size exclusion HPLC on analytical Zorbax GF-450 and GF-250 columns in series. These were developed with a 30 min isocratic gradient of 0.2M phosphate pH 7.0+10% ethanol at 1 ml/min and Fab detected using absorbance at 214 nm and 280 nm.

The MS model, experimental autoimmune encephalomyelitis (EAE), was used essentially as described by Baker et al., 1990. Journal of Neuroimmunology, 28:261-270.

Female ABH mice 8-10 weeks of age (Harlan) were immunised with mouse spinal cord homogenate (SCH, 3.33 mg/ml) in complete Freund's adjuvant in two sites, sc, on the flanks (150 µl/site) on days 0 and 7.

Four groups were dosed prior to onset of first relapse (during remission). Groups were assigned as follows—
Group 1 (n=11) anti-mouse IL17 Ab#13 Fab-di-PEG (100 mg/kg, s.c, weekly)
Group 2 (n=11) anti-mouse IL17 Ab#13 Fab-di-PEG (30 mg/kg, s.c, weekly)
Group 3 (n=9) anti-mouse IL-17 Ab#13 mIgG1 (10 mg/kg, sc)
Group 4 (n=9) PBS control Weights and clinical scores were recorded daily and terminal EDTA-Plasma collected.

Clinical Score Scale

| | |
|---|---|
| 0 | Normal |
| 0.25 | Tail dragging |
| 0.5 | Partial tail paralysis |
| 1 | Complete tail paralysis |
| 2 | Incomplete hind limb paralysis/loss of righting reflex |
| 3 | Complete hind paralysis/incontinence |
| 4 | Front limb paralysis/moribund |

Statistics

Pair wise comparisons of maximum and cumulative clinical scores and day of onset were performed using Mann-Whitney U test. Cumulative clinical score is defined as the sum of clinical scores throughout the disease course for each animal (area under the curve). Comparisons of disease incidence were performed using Fishers Exact Test. Maximum weight loss was analysed using one-way Anova with Bonferroni post test.

Results

FIG. 7*a* shows the effect of anti-IL17 Ab#13 di Fab-PEG and Ab#13 mIgG1 on clinical disease when dosed from remission (black arrowheads represent dosing days). When dosed prior to first relapse all active doses showed a significant reduction in cumulative and maximum clinical score and incidence.

FIG. 8 shows that during the acute phase, prior to antibody treatment, all assigned groups showed no significant differences in disease onset or clinical severity prior to antibody dosing.

FIG. 9 shows that anti-mouse IL-17 antibodies dosed prior to relapse onset during remission showed a significant reduction in maximum clinical score (Ab#13 di Fab-PEG 100 mg/kg vs. PBS p<0.05 and IL-17 Ab#13 mIgG1 vs. PBS p<0.001), There was also a reduction in cumulative score (Ab#13 di Fab-PEG (100 mg/kg and 30 mg/kg) and Ab#13 mIgG1 vs. PBS p<0.01, p<0.05 and p<0.001 respectively). Furthermore there was a reduction in maximum weight loss (Ab#13 di Fab-PEG 100 mg/kg and Ab#13 mIgG1 vs. PBS both p<0.05).

Actual incidence of relapse is summarised in table 1, with all actively treated groups having significantly lower incidence than the PBS control group.

TABLE 1

|  | Ab#13 di Fab-PEG 100 mg/kg*** | Ab#13 di Fab-PEG 30 mg/kg* | Ab#13 IgG1 10 mg/kg*** | PBS |
|---|---|---|---|---|
| Animals entering relapse | 0 | 2 | 0 | 7 |
| Animals not entering relapse | 11 | 9 | 11 | 2 |
| Total number of animals | 11 | 11 | 11 | 9 |

***P = 0.005
*p = 0.0216
***P = 0.005

Summary

Anti-mouse IL17 antibodies (Ab#13 di Fab-PEG and Ab#13 mIgG1) were dosed in a dose dependent manner during the remission phase prior to onset of first relapse. Effects were pronounced with a significant reduction for both antibodies in relapse incidence and upon maximum and cumulative disease score in comparison to the PBS control group.

Example 4

Effect of Ab#13 mIgG1 on the Symptoms of Chronic EAE in C57Bl/6 Mice

The chronic EAE model used was essentially as described by Copray et al., 2004. Journal of Neuroimmunology, 148: 41-53.

Female C57Bl/6 mice 6-8 weeks of age (Charles River) were immunised with Myelin Oligodendrocyte Protein (MOG 35-55, 0.66 mg/ml) in complete Freund's adjuvant (0.4 mg/ml *Mycobacterium*; 4:1 *M. tuberculosis: M butyricum*) in two sites, s.c, on the flanks (150 µl/site) on days 0 and 7. Mice were also administered pertussis toxin (1 µg/ml) on days 0, 1, 7, 8; 200 µl i.p Two groups were dosed prophylactically (10 mg/kg; s.c; commencing on PSD-1 until the end of experiment). One group (n=15) was dosed with Ab#13 mIgG1, (chimeric rabbit V region, Murine constant region IgG-1, as described in Example 1), the other (n=15) with 101.4 (Murine IgG-1 isotype control, 101.4).

Two groups were dosed therapeutically (upon 50% incidence) with Ab#13 mIgG1 and control antibody 101.4 (10 mg/kg; s.c commencing PSD 16 till end of experiment) Weights and clinical scores were recorded daily and terminal EDTA-Plasma collected.

Clinical Score Scale

| 0 | Normal |
|---|---|
| 0.25 | Tail dragging |
| 0.5 | Partial tail paralysis |
| 1 | Complete tail paralysis |
| 2 | Incomplete hind limb paralysis/loss of righting reflex |
| 3 | Complete hind paralysis/incontinence |
| 4 | Front limb paralysis/moribund |

Statistics

Statistical analysis was performed as described in Example 3.

Results

FIG. 10 shows that prophylactic dosing (a) of Ab#13 mIgG1 elicited significant delay in the onset of disease, cumulative and maximum clinical score. Therapeutic dosing (b) significantly reduced cumulative clinical score. Further analysis showed Ab#13 mIgG1 dosed prophylactically had significant effects in reducing cumulative score (p=0.0006), delay of onset (p=0.0184) and maximum clinical score (p=0.0032, all Mann-Whitney U test) (FIG. 11). Ab#13 mIgG1 dosed therapeutically also showed a significant reduction in cumulative score (b, p=0.0229, Mann-Whitney U test; FIG. 12).

Summary

Anti-mouse IL17 antibody Ab#13 mIgG1 was dosed in separate experiments prophylactically and therapeutically. Effects were most pronounced prophylactically with a significant reduction in maximum and cumulative disease score, furthermore incidence of disease was significantly delayed. Therapeutic treatment showed a reduction in cumulative disease score.

The invention claimed is:

1. A method for the treatment of multiple sclerosis (MS) comprising administering to a patient in need thereof a therapeutically effective amount of a neutralizing anti-IL-17 antibody or a neutralizing anti-IL-17 antibody fragment.

2. The method according to claim 1, wherein the neutralizing antibody or neutralizing antibody fragment is monoclonal, polyclonal, chimeric, humanized, or bispecific.

3. The method according to claim 1, wherein the neutralizing antibody fragment is a Fab, Fab', F(ab')$_2$, scFv or epitope binding fragment.

4. The method according to claim 1, wherein the neutralizing antibody or neutralizing antibody fragment is conjugated to one or more effector molecule(s).

* * * * *